United States Patent
Hamatani et al.

(10) Patent No.: US 7,963,145 B2
(45) Date of Patent: Jun. 21, 2011

(54) APPARATUS AND METHOD FOR DETECTING COMBUSTIBLE GAS WITHIN ATMOSPHERE TO BE DETECTED

(75) Inventors: Shogo Hamatani, Nagoya (JP); Shoji Kitanoya, Kasugai (JP); Ryuji Inoue, Tajimi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 729 days.

(21) Appl. No.: 12/015,699

(22) Filed: Jan. 17, 2008

(65) Prior Publication Data

US 2008/0282771 A1 Nov. 20, 2008

(30) Foreign Application Priority Data

Jan. 23, 2007 (JP) ................................. 2007-012831

(51) Int. Cl.
*G01N 25/00* (2006.01)
*G01N 27/18* (2006.01)
(52) U.S. Cl. ...................... 73/23.31; 73/25.05; 73/31.05
(58) Field of Classification Search ................... 73/23.2, 73/25.05, 23.31, 31.05
See application file for complete search history.

(56) References Cited

U.S. PATENT DOCUMENTS

| | | | | |
|---|---|---|---|---|
| 5,780,715 | A | * | 7/1998 | Imblum ....................... 73/23.21 |
| 5,922,287 | A | * | 7/1999 | Kato et al. ....................... 422/95 |
| 6,812,708 | B2 | * | 11/2004 | Bristol ........................... 324/431 |

FOREIGN PATENT DOCUMENTS

| | | | |
|---|---|---|---|
| JP | 2005-461561 | * | 6/2005 |
| JP | 2006-10670 A | | 1/2006 |
| JP | 2007-10594 | * | 1/2007 |

* cited by examiner

*Primary Examiner* — Daniel S Larkin
(74) *Attorney, Agent, or Firm* — Sughrue Mion, PLLC

(57) ABSTRACT

In apparatus and method for detecting a combustible gas within an atmosphere to be detected, a calculated humidity deviation corresponding to a past gas concentration stored in a memory unit of a microcomputer is calculated on the basis of a correlation between a preset gas concentration of the combustible gas and the calculated humidity deviation, a calculated humidity of the atmosphere to be detected is corrected using the calculated humidity deviation to calculate a corrected humidity, and, when a concentration of the combustible gas is calculated on the basis of a terminal voltage, a temperature of the atmosphere to be detected, and a humidity of the atmosphere to be detected, the calculated corrected humidity is used for the humidity of the atmosphere to be detected calculated on the basis of terminal voltages across first and second heating resistors and the temperature of the detected temperature.

17 Claims, 7 Drawing Sheets

APPARATUS AND METHOD FOR DETECTING COMBUSTIBLE GAS WITHIN ATMOSPHERE TO BE DETECTED

BACKGROUND OF THE INVENTION

1. Field of the Invention

The present invention relates to apparatus and method for detecting a combustible gas within an atmosphere to be detected (hereinafter also called, combustible gas detecting apparatus and method) and, more particularly, relates to the apparatus and method for detecting the combustible gas within the atmosphere to be detected, equipped with a plurality of heating resistors disposed within the atmosphere to be detected.

2. Description of the Related Art

A Japanese Patent Application Publication (tokkai) No. 2006-10670 published on Jan. 12, 2006 exemplifies a previously proposed combustible gas detecting apparatus. In the previously proposed combustible gas detecting apparatus disclosed in the above-described Japanese Patent Application Publication, the combustible gas within the atmosphere to be detected is detected using each of terminal voltages across respective heating resistors which are controlled to provide mutually different temperatures.

In detail, in the previously proposed combustible gas detecting apparatus disclosed in the above-described Japanese Patent Application Publication, the combustible gas is detected on the basis of a relationship among respective terminal voltages across the respective heating resistors, a temperature of the atmosphere to be detected, and a humidity of the atmosphere to be detected.

It should be noted that the humidity of the atmosphere to be detected can be calculated on the basis of a relationship between the respective terminal voltages across the respective heating resistors and the temperature of the atmosphere to be detected.

SUMMARY OF THE INVENTION

However, in the previously proposed combustible gas detecting apparatus disclosed in the above-described Japanese Patent Application Publication, premising that a concentration of combustible gas is a predetermined reference value (for example, 0%), the humidity (calculated value) of the atmosphere to be detected is calculated on the basis of the relationship between each of the terminal voltages and the temperature of the atmosphere to be detected. Hence, a deviation (calculated humidity deviation) in the humidity (calculated value) of the atmosphere to be detected due to the variation in the concentration of combustible gas often occurs. Then, there is a possibility that a detection accuracy of combustible gas is reduced due to the calculation deviation of the humidity if the calculated humidity deviation in the humidity (a calculation deviation) of the atmosphere to be detected occurs.

In other words, even if the humidity (actual value) of the atmosphere to be detected is constant, in a case where the concentration of combustible gas is varied to a value different from the predetermined reference value, the humidity (calculation value) is often varied which is determined on the basis of the relationship between each of the terminal voltages and the temperature of the atmosphere to be detected.

In this way, in a case where the deviation occurs in the humidity (calculation value) obtained through the calculation even if the actual humidity is constant. It is, hence, an object of the present invention to provide combustible gas detecting apparatus and method which can suppress the reduction of the detection accuracy of combustible gas and in which the deviation in the humidity (calculation deviation) obtained by the calculation is difficult to occur even if the concentration of combustible gas is varied in an actual use.

According to one aspect of the present invention, there is provided an apparatus for detecting a combustible gas within an atmosphere to be detected, comprising: first and second heating resistors disposed within the atmosphere to be detected; a power supply control section configured to perform a power supply control for first and second heating resistors in order for the first and second heating resistors to provide resistance values corresponding to mutually different target temperatures; a temperature detecting section configured to detect a temperature of the atmosphere to be detected; a voltage detecting section configured to detect each of terminal voltages across the first and second heating resistors; a humidity calculating section configured to calculate a humidity of the atmosphere to be detected on the basis of the respective terminal voltages detected by the voltage detecting section and the temperature detected by the temperature detecting section; a concentration calculating section configured to calculate a gas concentration of the combustible gas in the atmosphere to be detected on the basis of the terminal voltage including at least one of the two terminal voltages detected by the voltage detecting section, the humidity calculated by the humidity calculating section, and the temperature detected by the temperature detecting section; a gas concentration storing section configured to store the gas concentration calculated by the concentration calculating section therein; and a humidity correcting section configured to calculate a calculated humidity deviation corresponding to a past gas concentration stored in the gas concentration storing section on the basis of a preset correlation between the concentration of the combustible gas and the calculated humidity deviation of the humidity calculating section and to correct the humidity of the atmosphere to be detected calculated by the humidity calculating section using the calculated humidity deviation to calculate a corrected humidity, the concentration calculating section using the corrected humidity calculated by the corrected humidity calculating section for the humidity calculated by the humidity calculating section.

According to another aspect of the present invention, there is provided with a method for detecting a combustible gas within an atmosphere to be detected, comprising: providing first and second heating resistors disposed within the atmosphere to be detected; performing a power supply control for first and second heating resistors in order for the first and second heating resistors to provide resistance values corresponding to mutually different target temperatures; detecting a temperature of the atmosphere to be detected; detecting each of terminal voltages across the first and second heating resistors; calculating a humidity of the atmosphere to be detected on the basis of the detected respective terminal voltages and the detected temperature; calculating a gas concentration of the combustible gas in the atmosphere to be detected on the basis of the terminal voltage including at least one of the detected two terminal voltages, the calculated humidity, and the detected temperature; storing the calculated gas concentration therein; calculating a calculated humidity deviation corresponding to a stored past gas concentration on the basis of a preset correlation between the gas concentration of the combustible gas and the calculated humidity deviation; and correcting the calculated humidity of the atmosphere to be detected using the calculated humidity deviation to calculate a corrected humidity, at the concentration calculating, the calculated corrected humidity being used for the calculated humidity at the humidity calculating.

According to the present invention, since the corrected humidity obtained by the humidity correcting section using the concentration of the combustible gas calculated in the past is a calculated value on which an influence of the concentration of the combustible gas in the atmosphere to be detected is reflected, the corrected humidity provides a value more approximate to the actual humidity than the humidity which is the direct result of calculation by the humidity calculating section. In other words, the corrected humidity provides the value having a small deviation to the actual humidity as compared with the result of calculation of the humidity by the humidity calculating section. Thus, since the concentration calculating section uses the corrected humidity calculated by the humidity calculating section as the humidity calculated by the humidity calculating section when executing the calculation of the concentration of the combustible gas in the atmosphere to be detected, the concentration of the combustible gas can be detected while suppressing the detection deviation of the humidity due to the influence of the combustible gas. That is to say, the detection deviation of the concentration of the combustible gas caused by the detection deviation of the humidity can be suppressed and the reduction of a detection accuracy of the concentration of the combustible gas can be suppressed. Even if the combustible gas concentration is varied, according to the present invention, the deviation in the humidity (the calculation value) obtained by the calculation is difficult to occur and the combustible gas detecting apparatus which can suppress the reduction of the combustible gas detection accuracy can be realized. It should be noted that, as the two terminal voltages detected by the voltage detecting section, the terminal voltage across one (a higher-temperature heating resistor) of the first and second heating resistors for which the power supply control is performed to provide a resistance value corresponding to a higher target temperature and that across the other (a lower-temperature heating resistor) of the first and second heating resistors for which the power supply control is performed to provide the resistance value corresponding to a lower target temperature are present. Thus, the concentration calculating section can use any one of only the terminal voltage across the higher-temperature heating resistor, only the terminal voltage across the lower-temperature heating resistor, a difference value (voltage difference) between the terminal voltage across the higher-temperature heating resistor and that across the lower-temperature heating resistor, and a ratio (voltage ratio) between the terminal voltage across the higher-temperature heating resistor and that across the lower-temperature heating resistor, and so forth since the terminal voltage used to calculate the gas concentration includes at least one of the two terminal voltages.

DETAILED DESCRIPTION OF THE INVENTION

Reference will hereinafter be made to the drawings in order to facilitate a better understanding of the present invention.

A combustible gas detecting apparatus 1 to which the present invention is applicable is equipped with a gas detection element 60 which is a thermal conductive gas detection element. Combustible gas detecting apparatus 1 detects a concentration of a combustible gas.

This combustible gas detecting apparatus 1 is, for example, mounted in a piping structure equipped in a fuel cell unit of an automotive vehicle and is used for detecting hydrogen included in a detected gas exhausted through the piping structure. In addition, combustible gas detecting apparatus 1 includes a control circuit 200 and a microcomputer 94 in combustible gas detecting apparatus 1 to detect a combustible gas included in the detected gas.

Figure 1:
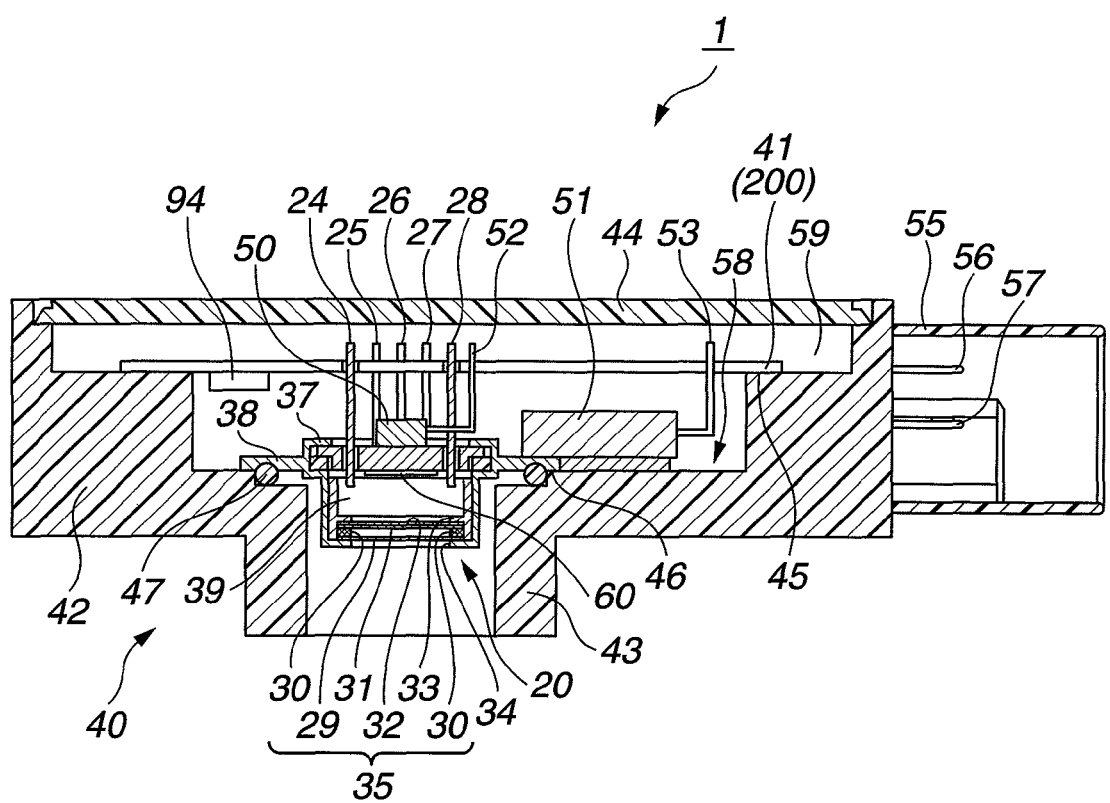
FIG. 1 is a cross sectional view of a combustible gas detecting apparatus in a first preferred embodiment according to the present invention.
Figure 2A:
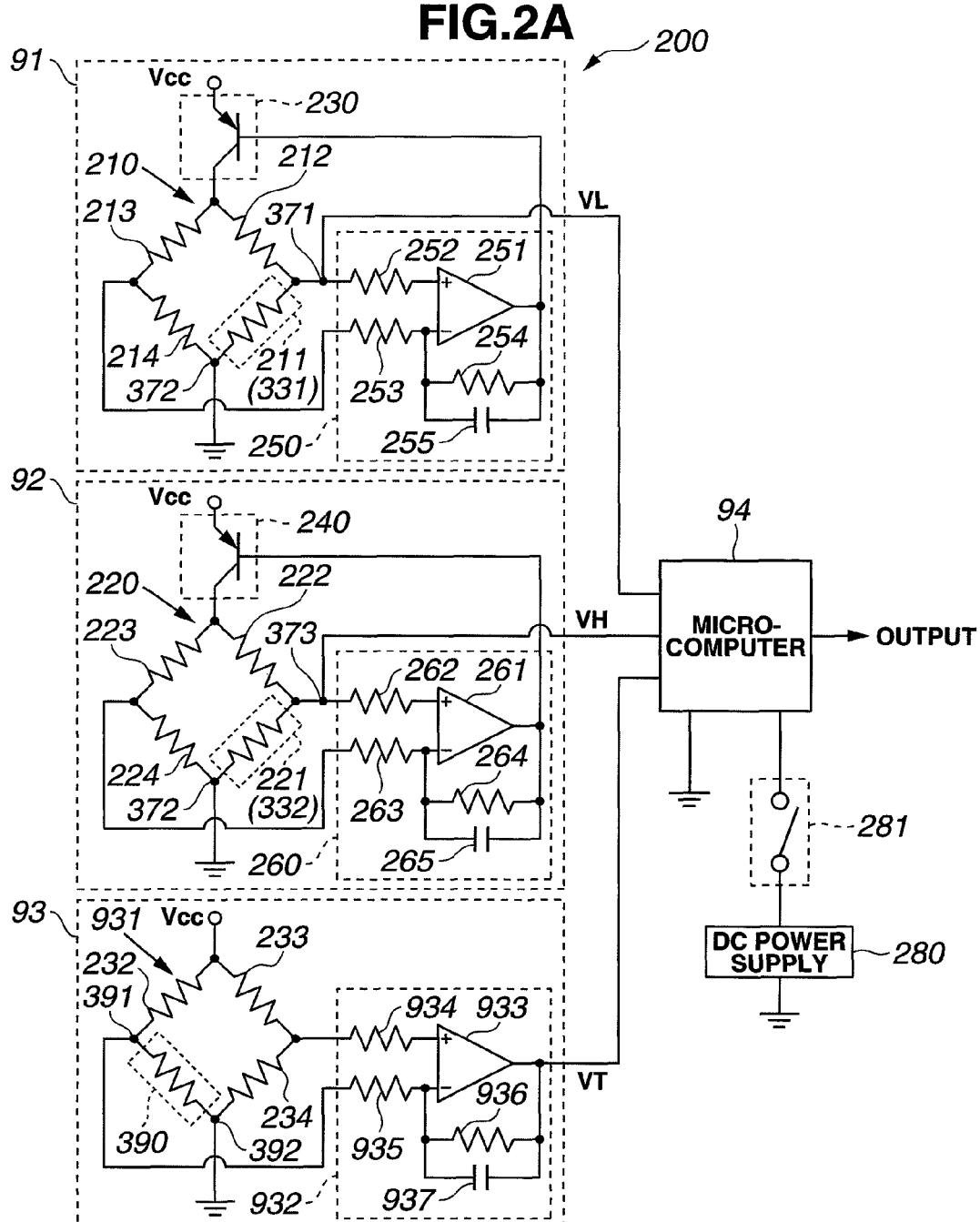
FIG. 2A is a block diagram of a control circuit and a microcomputer in the first embodiment of the combustible detecting apparatus according to the present invention shown in FIG. 1.
Figure 2B:
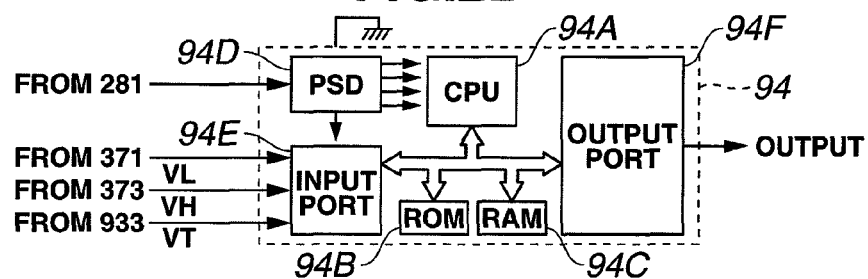
FIG. 2B is a block diagram representing an internal structure of the microcomputer shown in FIG. 2A.

Then, FIG. 1 shows a cross sectional view of combustible gas detecting apparatus 1. FIGS. 2A and 2B show a schematic block diagram of a control circuit 200 and a microcomputer 94 in the combustible gas detecting apparatus 1 shown in FIG. 1 and a schematic block diagram of microcomputer 94 shown in FIG. 2A, respectively.

As shown in FIG. 1, combustible gas detecting apparatus 1 includes: an element casing 20 in which a gas detection element 60 to detect a gas to be detected is housed; and a housing 40 which supports element casing 20 and in which a circuit board 41 connected electrically to gas detection element 60 is housed.

It should be noted that a vertical direction in FIG. 1 is a vertical direction in combustible gas detecting apparatus 1 and a horizontal direction in FIG. 1 is a horizontal direction in combustible gas detecting apparatus 1. First, a structure of housing 40 will be explained with reference to FIG. 1.

Housing 40 includes: a casing main frame 42; and a case lid 44 which encloses an opening disposed on an upper end part of casing main frame 42. In addition, in housing 40, a circuit board 41, microcomputer 94, and heating resistors 50, 51 are equipped. Each member constituting housing 40 will herein be described in details.

Casing main frame 42 is a vessel having openings on upper and lower surfaces thereof and having a predetermined height. Casing main frame 42 includes: a holding part 46 which holds an alligator part 38 of element casing 20; and a circuit board holding part 45 holding a peripheral part of circuit board 41. The opening equipped on the upper surface of casing main frame 42 is structured to enable a disposition of case lid 44 made of a synthetic resin to enclose the opening on the upper surface of casing main frame 42.

In addition, casing main frame 42 includes: a flow path forming part 43 formed on a lower center of casing main frame 42; and a connector 55 formed on a side part of casing main frame 42 to receive a power supply from an external. An introducing part 35 of element casing 20 to introduce and exhaust the detected gas is housed in an inside of flow path forming part 43. As described above, element casing 20 is held by a holding part 46 in a state in which part of element casing 20 is disposed within housing 40. A seal member 47 is disposed to seal (hermetically seal) a gap between these alligator part 38 of element casing 20 and casing main frame 42 thereof.

Connector 55 serves as a power transmitting member to supply electricity to circuit board 41 and microcomputer 94 and assembled onto an outer side surface of casing main frame 42. Respective connector pins 56, 57 are electrically connected to circuit board 41 and microcomputer 94 via a wiring (not shown) buried into a sidewall of casing main frame 42.

Circuit board 41 is a plate-like board having a predetermined thickness and includes control circuit 200 (refer to FIG. 2A) to detect the combustible gas included in the detected gas and a temperature control circuit (not shown) to control temperatures of heating resistors 50, 51.

This control circuit 200 is electrically connected to respective electrodes of gas detection element 60 (electrode films 371, 373, 391 and grounded electrode films 372, 392 as will be described later (refer to FIGS. 2A and 5)), respectively. Lead wires 52, 53 are electrically connected between the temperature control circuit and heating resistors 50, 51. It should be noted that lead wires 52, 53 have two wires, respectively. A structure of control circuit 200 equipped on circuit board 41 will be described later.

Microcomputer 94 equipped on a lower surface of circuit board 41 executes various processes such as a process (a sensor output calculation processing) to calculate a concentration of the combustible gas included in the detected gas and a process (s temperature control processing) to control heat generation quantities (temperatures) of heating resistors 50, 51 on the basis of the output of the temperature control circuit. This microcomputer 94 includes at least functionally a memory unit configured to store programs to execute these sensor output calculation processing and temperature control processing of heating resistors 50, 51 and a CPU (Central Processing Unit) 94A configured to execute the programs stored in the memory unit.

Next, heating resistors 50, 51 will be described below with reference to FIG. 1. Heating resistors (or called, heat generating elements) 50, 51 serve to heat element casing 20 via housing 40 or directly to hold an internal temperature of element casing 20 at a temperature higher than a dew point. Heating resistors (elements) 50, 51 are, for example, constituted by resistors used in electronic parts and so forth or film heaters.

Heating resistors 50, 51 are preferably disposed at a position at which heat can be transferred to a member contacting a space to be detected 39 (or called, detected space) from among housing space forming surfaces 58 enclosing a housing space 59 in order to heat efficiently the internal surface of element casing 20 forming space to be detected 39. Or heating resistors 50, 51 are preferably disposed at the position at which heat can efficiently be transmitted to element casing 20 which is a member contacting space to be detected 39. For example, heating resistors 50, 51 can be disposed on a part of element casing 20 which constitutes housing space forming surfaces 58 or can be disposed at a region of the internal surface of housing casing 40 adjacent to element casing 20 constituting housing space forming surfaces 58 (the same surface as the surface on which holding part 46 is formed).

Heat generation quantities of heating elements (resistors) 50, 51 are preferably set for the temperature of the internal surface of element casing 20 on which space to be detected 39 is formed to be higher than the dew point of the detected gas. Thus, the detected gas is cooled to a temperature point equal to or lower than the dew point of the detected gas at the internal surface of element casing 20 so as to enable a prevention of the detected gas from being bedewed within space to be detected 39. In addition, since the detected gas has ordinarily a temperature higher than the dew point, temperatures of heating elements 50, 51 are preferably set to temperatures equal to or higher than the temperature of the gas to be detected. Such a temperature setting as described above can cool the detected gas at the internal surface of element casing 20 forming space to be detected 39 of gas to be detected and can prevent the temperature of the gas to be detected from becoming unstable.

Thus, combustible gas detecting apparatus 1 can reduce an influence of a temperature characteristic of gas detection element 60 along with a variation in the temperature of the gas to be detected and can detect the combustible gas included in the gas to be detected with a high accuracy.

These heating elements 50, 51 are controlled, for example, by means of a well known constant voltage control, a constant power control, or a PWM (Power Width Modulation) control. It should be noted that the control method in a case where a plurality of heat generating elements such as heating elements (resistors) 50, 51 are installed may adopt the same control method for each heating element or may adopt the different methods for the respective heating elements 50, 51. In addition, the program prescribing the control method for heating elements 50, 51 is stored in the memory unit with which microcomputer 94 is provided and executed by CPU 94A.

Figure 3:
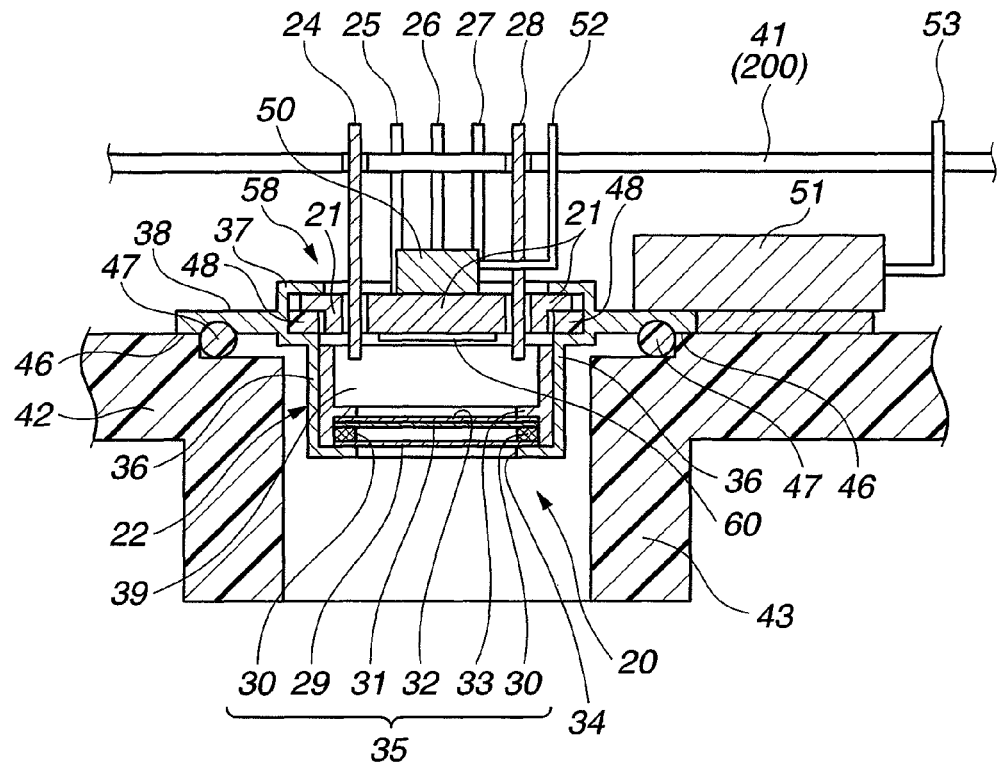
FIG. 3 is an expanded and longitudinal cross sectional view of a surrounding part of an element casing of the combustible gas detecting apparatus.

Next, element casing 20 constituting combustible gas detecting apparatus 1 will be described with reference to FIG. 3. FIG. 3 shows a longitudinal cross sectional view in which a surrounding part of element casing 20 of combustible gas detecting apparatus 1 is expanded. It should be noted that the vertical direction of combustible gas detecting apparatus 1 in FIG. 3 is the vertical direction of combustible gas detecting apparatus 1 and the horizontal direction in FIG. 3 is the horizontal direction of combustible gas detecting apparatus 1.

As shown in FIG. 3, element casing 20 includes: a connecting terminal attaching bed 21 on which gas detection element 60 is equipped; and a detected space forming member 22 having a cylindrical wall surface grasping a peripheral edge part of connecting terminal attaching bed 21 and projected toward an introduction inlet introducing the detected gas. Inserting holes to insert individually and independently connecting terminals 24 to 28 are installed on connecting terminal attaching bed 21 and a peripheral edge part of each inserting hole is covered with an insulative member.

This connecting terminals 24 to 28 are members to connect electrically gas detection element 60 to circuits installed on circuit board 41. These connecting terminals 24 to 28 are formed in a form of bars made of electrically conductive members. Each one end of connecting terminals 24 to 28 is inserted into an inserting hole installed on connecting terminal attaching bed 21 and is vertically supported with respect to connecting terminal attaching hole 21.

On the other hand, detected space forming member 22 includes: an outer envelope 36 on an outer side surface of which the detected gas is contacted; an attaching bed supporting part 37 which grasps a peripheral edge part of connecting terminal attaching bed 21; and alligator part 38 supported by housing 40. In addition, an introduction inlet 34 which is an opening for introducing the detected gas into space to be detected 39 is installed on a lower end portion of detected space forming member 22.

An introducing part 35 forming a flow passage to introduce and exhaust the gas to be detected to and from gas detection element 60 is installed at the adjacent part of introduction inlet 34. Then, a water repellent filter 29, a spacer 30, and two sheets of metal wirings 31, 32 are filled in introducing part 35 in a sequence nearer to introduction inlet 34, respectively. In addition, these members are grasped and fixed by means of detected space forming member 22 and a filter fixture member 33. Herein, the member constituting introducing part 35 will, hereinbelow, be described in details.

Water repellent filter 29 is a filter attached at a position nearest to introduction inlet 34 and is a thin film having a repellency removing water droplets included in the detected gas. Thus, under a moisture environment in which the water droplets come flying, water repellent filter 29 can prevent gas detection element 60 from being water bathed. Water repellent filter 29 may be any type filter which can remove water droplets due to a physical adsorption. For example, a filter utilizing a polytetrafluoroethylene (PTFE) may be applied to water repellent filter 29.

Spacer 30 is equipped on an inner peripheral wall of filter fixture member 33 and is a member in a form of opening in which gas to be detected is introduced (a ring shape in a plan view). Spacer 30 has a predetermined thickness to adjust a position thereof between water repellent filter 29 and two sheets of wire nettings 31, 32.

Wire nettings 31, 32 are provided with predetermined thicknesses and predetermined openings. Even if a temperature of each heating resistor 50, 51 is raised to a temperature higher than an ignition temperature of hydrogen gas included in the gas to be detected to ignite hydrogen gas, wire nettings 31, 32 perform a function as flame arresters to prevent a flame from being taken out to the external of element casing 20.

Filter fixture member 33 is a member for grasping water repellent filter 29, spacer 30, and two sheets of wire nettings 31, 32 together with detected space forming member 33. Filter fixture member 33 has a cylindrical wall surface to be contacted against the inner wall surface of detected space forming member 22 and has a convex part projected toward an inner direction of the wall surface from the inner surface of the cylindrical wall surface. It should be noted that the convex part of filter fixture member 33 for grasping water repellent filter 29, spacer 30, and two sheets of metal nettings 31, 32 together with detected space forming member 22.

Figure 4:
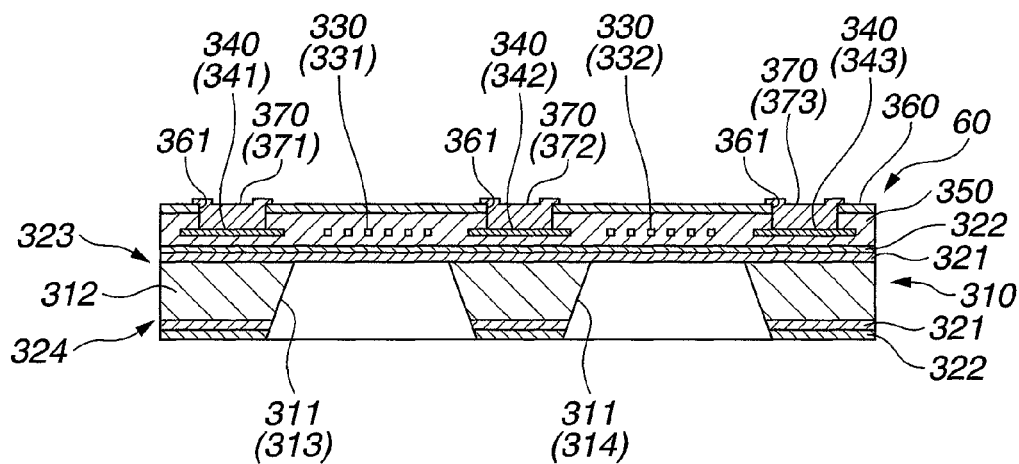
FIG. 4 is a cross sectional view in an arrow marked direction cut away along a line A—A of a combustible gas detection element shown in FIG. 5.
Figure 5:
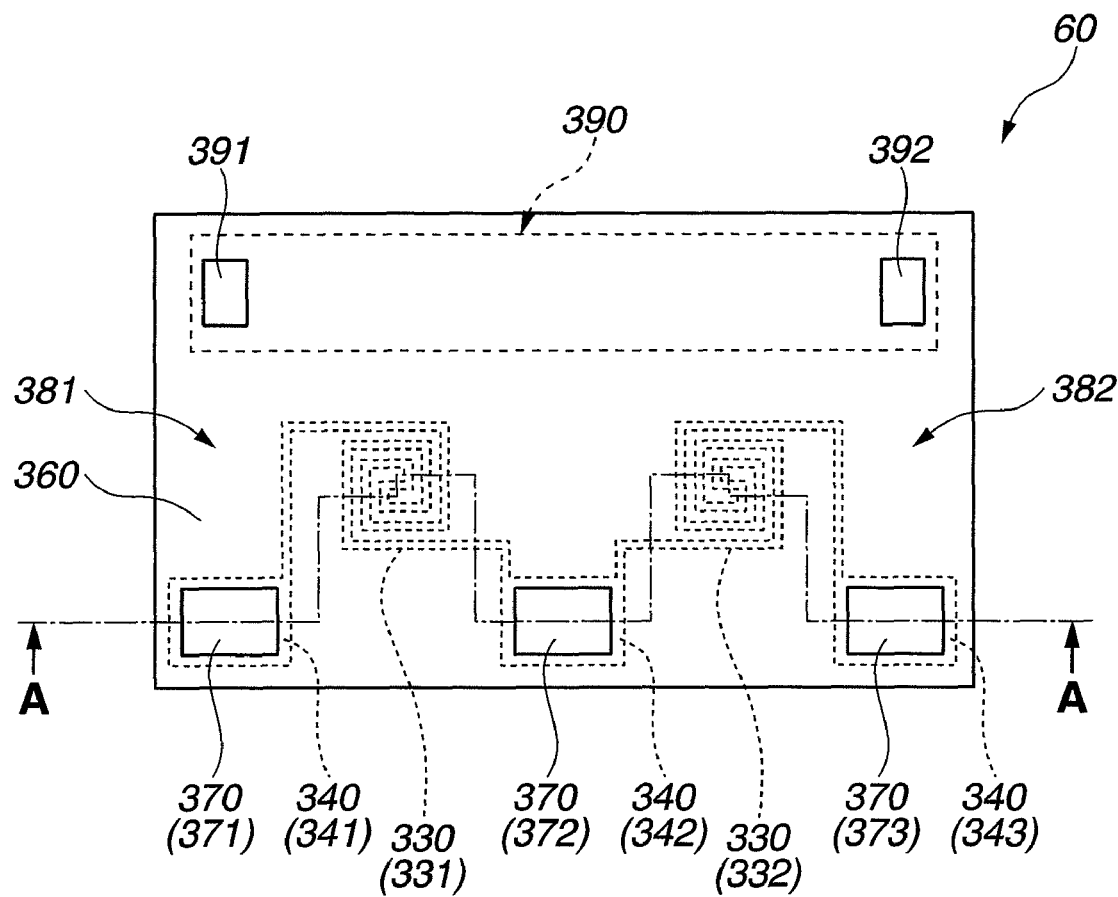
FIG. 5 is a plan view of the gas detection element

Next, a structure of gas detection element 60 described above will be described below. FIG. 4 shows a cross sectional view of gas detection element 60. FIG. 5 shows the plan view of gas detection element 60. It should be noted that FIG. 4 shows the cross sectional view in an arrow-marked direction of gas detection element 60 in FIG. 5 cut away along line A-A of FIG. 5.

Gas detection element 60 is manufactured using a micromachining technique and includes, as shown in FIG. 4, a silicon made semiconductor substrate 310; and insulating layers attached onto both upper and lower sides of silicon made semiconductor substrate 310 (upper insulating layer 323 and lower insulating layer 324). Upper insulating layer 323 is formed on a front surface of silicon made semiconductor substrate 310. On the other hand, lower insulating layer 324 is formed on a rear surface of silicon made semiconductor substrate 310.

It should be noted that upper insulating layer 323 includes: a silicon oxide film 321 formed on the front surface of silicon made semiconductor substrate 310; and silicon nitride film 322 laminated on silicon oxide film 321. In addition, lower insulating layer 324 includes: oxide silicon film 321 formed on the rear surface of silicon made semiconductor substrate 310 and silicon nitride film 322 laminated on silicon oxide film 321.

A plurality of recess parts 311 are formed at a predetermined interval of distance on the rear surface of upper insulating layer 323. In addition, positions corresponding to recess parts 311 are removed from lower insulating layer 324 and are formed as opening portions of recess parts 311. Thus, upper insulating layer 323 is exposed to the external through the opening portions corresponding to respective recess parts 311. It should be noted that silicon made semiconductor substrate 310 constitutes substrate parts 312 at positions of silicon made semiconductor substrate other than respective recess parts 311.

Gas detection element 60 further includes, as shown in FIGS. 4 and 5, first and second heating resistors 330 disposed on the left and right sides of gas detection element 60 (a left-side heating resistor 331 and a right-side heating resistor 332) and a plurality of wiring films 340 disposed on the left side, a center side, and a right side of gas detection element 60 (a left-side wiring film 341, a center-side wiring film 342, and a right-side wiring film 343).

Left-side heating resistor 331 is formed in a spiral shape on a position corresponding to a left-side recess part 313 of the front surface of upper insulating layer 323. On the other hand, right-side heating resistor 332 is formed in the spiral shape on a position corresponding to a right-side recess part 314 from the surface of upper insulating layer 323. First and second heating resistors 330 (left-side heating resistor 331 and right-side heating resistor 332) are made of platinum materials in the same way as each wiring film 340 (left-side wiring film 341, center-side wiring film 342, and right-side wiring film 343).

Left-side wiring film 341, as shown in FIG. 4, is formed on a left side portion of the front surface of upper insulating layer 323 and is located to correspond to substrate part 312 of silicon made semiconductor substrate 310 and is formed to electrically be connected to one end of right-side heating resistor 331, as shown in FIG. 5. Center-side wiring film 342 is positioned at the center part of the front surface of upper insulating layer 323 to correspond to substrate part 312 of silicon made semiconductor substrate 310. In addition, right-side wiring film 343 is positioned at a right-side portion of the surface of upper insulating layer 323 to correspond to substrate part 312 of silicon made semiconductor substrate 310 and is formed to be electrically connected to the other end of right-side heating resistor 332.

In addition, gas detection element 60 is provided with an inner protective layer 350 and an outer protective layer 360, as shown in FIGS. 4 and 5. and is provided with three electrode films 370 (a left-side electrode film 371, a center-side electrode film 372, and a right-side electrode film 373). Inner protective layer 350 is formed on the surface of upper insulating layer 323 to enclose each wiring film 340 and each heating resistor 330. In addition, outer protective layer 360 is laminated on inner protective layer 350.

Next, left-side, center-side, and right-side contact holes 361 are formed on respective positions corresponding to left-side, center-side, and right-side wiring films 340 from among inner protective layer 350 and outer protective layer 360. Thus, left-side, center-side, and right-side wiring films 340 (left side wiring film 341, center side wiring film 342, and right side wiring film 343) are enabled to be electrically connected to the external of inner protective layer 350 and outer protective layer 360 via left-side, center-side, and right-side contact holes 361.

Left-side, center-side, and right-side electrode films 370 (left-side electrode film 371, center-side electrode film 372, right-side electrode film 373) are formed on left-side, center-side, and right-side contact holes 361. Left-side, center-side, and right-side electrode films 370 (left-side electrode film 371, center-side electrode film 372, and right-side electrode film 373) are electrically connected to left-side, center-side, and right-side wiring films 340 (left-side wiring film 371, center-side wiring film 372, and right-side wiring film 373) respectively.

In this embodiment, in gas detection element 60, left-side heating resistor 331, each wiring film 340 at the left side and the center side (left-side wiring film 341, center-side wiring film 342), and left-side and center-side electrode film 370 (left-side electrode film 371, center-side electrode film 372) mainly constitute a left-side thermal conduction type gas detecting part 381. In addition, right-side heating resistor 332 and center-side and right-side wiring films 340 (center-side wiring film 342 and right-side wiring film 343) and center-side and right-side electrode films 370 (center-side electrode film 342 and right-side wiring film 343) and center-side and right-side electrode films 370 (center electrode film 372 and right-side electrode film 373) mainly constitutes a right-side thermal conduction type gas detecting part 382.

In addition, gas detection element 60, as shown in FIG. 5, includes a temperature measuring resistor 390. This temperature measuring resistor 390 is formed of a temperature measuring resistance material including platinum (Pt) and is formed as a thin-film resistor between upper-side insulating film 323 and inner-side protective layer 350. Thus, temperature measuring resistor 390 detects a temperature of an atmosphere to be detected into which combustible gas detecting apparatus 1 is disposed. In this embodiment, a temperature resistance coefficient of temperature measuring resistor 390 is generally the same as each temperature resistance coefficient of first and second heating resistors 330. In addition, electrode film 391 and grounded electrode film 392 are formed within respective contact holes (not shown) formed on both left and right ends of temperature measuring resistors 390 from among inner protective layer 350 and outer protective layer 360. It should be noted that a temperature measuring resistor 390 is connected to circuit board 41 (control circuit 200) via electrode film 391, grounded electrode film 392, and a terminal (not shown).

Next, a rough structure of control circuit 200 described above will be explained with reference to FIG. 2A. Control circuit 200 includes a low-temperature-side gas detecting circuit 91, a high-temperature-side gas detecting circuit 92, and a temperature measuring circuit 93.

Low-temperature-side gas detecting circuit 91 includes a low-temperature-side bridge circuit 210. High-temperature-side gas detecting circuit 92 includes a high-temperature-side bridge circuit 220. Temperature measuring circuit 93 includes a temperature measuring bridge circuit 931.

Low-temperature-side bridge circuit 210 includes, as shown in FIG. 2A, a lower-temperature heating resistor 211 and three fixed resistors 212, 213, 214 to form a bridge circuit.

In low-temperature-side bridge circuit 210, lower-heating resistor 211 is constituted by left-side heating resistor 331 constituting left-side thermal conduction type gas detecting part 381 of gas detection element 60. One end of lower-temperature heating resistor 211 is grounded and the other end thereof is grounded via fixed resistors 212, 213, and 214.

In low-temperature-side bridge circuit 210, a controlled voltage is applied from a current adjustment circuit 230 to low-temperature-side bridge circuit 210 in order for a potential difference developed between a common terminal of lower-temperature heating resistor 211 and fixed resistor 212 and a common terminal of fixed resistor 213 and fixed resistor 214 to become zero. Consequently, a resistance value of lower-temperature heating resistor 211 is controlled to be constant and, in other words, the temperature of left-side heating resistor 331 is controlled to be constant. Then, the voltage developed on the common terminal to lower-temperature heating resistor 211 and fixed resistor 212 is inputted to microcomputer 94 as an output signal (potential VL).

Current adjustment circuit 230 forms the control voltage described above to low-temperature-side bridge circuit 210 using an output voltage Vcc of direct current (DC) power supply 280 to maintain the resistance value of lower-temperature heating resistor 211 at a value corresponding to a constant temperature (a lower temperature target temperature, for example, 150° C.) in accordance with an output of an operational amplifier circuit 250. It should be noted that the resistance value of lower-temperature heating resistor 211 is varied (increased or decreased) in accordance with a variation in the controlled voltage from current adjustment circuit 230 or the variation in temperature (rise or drop) of lower-temperature heating resistor 211.

It should be noted that operational amplifier circuit 250 includes an operational amplifier 251, a non-inverting input terminal connected resistor 252, an inverting input terminal connected resistor 253, a feedback resistor 254, and a capacitor 255.

On the other hand, high-temperature-side bridge circuit 220 includes, as shown in FIG. 2A, a higher-temperature heating resistor 221 and three fixed resistors 222, 223, and 224 to constitute another bridge circuit. In high-temperature-side bridge circuit 220, higher-temperature heating resistor 221 is constituted by right-side heating resistor 332 constituting right-side thermal conduction type gas detecting part 382 of gas detection element 60. It should be noted that one end of higher-temperature heating resistor 221 is grounded and the other end of this resistor 221 is grounded via fixed resistor 222, fixed resistor 223, and fixed resistor 224.

In high-temperature-side bridge circuit 220, the controlled voltage is applied from current adjustment circuit 240 in order for the potential difference developed between the common terminal to higher-temperature heating resistor 221 and fixed resistor 222 and the common terminal of fixed resistor 223 and fixed resistor 224 to become zero. Thus, the resistance value of higher-temperature heating resistor 221 is controlled to be constant. In addition, the voltage developed at the common terminal to higher-temperature heating resistor 221 and fixed resistor 222 is inputted to microcomputer 94 as an output signal (potential of VH).

Current adjustment circuit 240 forms the controlled voltage to high-temperature-side bridge circuit 220 using output voltage Vcc of direct current power supply 280 in order to maintain the resistance value of higher-temperature heating resistor 221 at a value corresponding to a constant temperature (a high temperature target temperature, for example, 330° C.) in accordance with an output of an operational amplifier circuit 260. It should be noted that the resistance value of higher-temperature heating resistor 221 is varied (increased or decreased) in accordance with the variation (rise or drop) in the controlled voltage from current adjustment circuit 240 or the variation (increase or decrease) in the temperature of higher-temperature heating resistor 221.

It should be noted that operational amplifier circuit 260 includes, as shown in FIG. 2A, an operational amplifier 261, a non-inverting input terminal connected resistor 262, an inverting input terminal resistor 263, a feedback resistor 264, and a capacitor 265.

Temperature measuring bridge circuit 931 includes, as shown in FIG. 2A, a temperature measuring resistor 390 and three fixed resistors 232, 233, and 234 to constitute still another bridge circuit.

In temperature measuring bridge circuit 931, temperature measuring resistor 390 shown in FIG. 2A is constituted by temperature measuring resistor (resistance element) 390 (refer to FIG. 5) of gas detection element 60.

Temperature measuring resistor 390 has one end grounded and the other end grounded via fixed resistor 233, fixed resistor 233, and fixed resistor 234. Temperature measuring bridge circuit 931 is operated when an output voltage Vcc of direct current (DC) power supply 280 is applied between a common terminal (an one end side power supply terminal) to temperature measuring resistor 390 and fixed resistor 232 and a common terminal (the other side power supply terminal) to fixed resistor 233 and fixed resistor 234.

Under this operation, temperature measuring bridge circuit 931 outputs the potential difference representing the value corresponding to the temperature of the atmosphere to be detected) developed between the common terminal (one end side output terminal to temperature measuring bridge circuit 931) to temperature measuring resistor 390 and fixed resistor 232 and the common terminal (the other end side output terminal of temperature measuring bridge circuit 931) to fixed resistor 233 and fixed resistor 234. In addition, one end output terminal and the other end output terminal of temperature measuring bridge circuit 931 are connected to an operational amplifier circuit 932.

Operational amplifier circuit 932 amplifies the potential difference developed between the one end side output terminal and the other end side output terminal of temperature measuring bridge circuit 931 and outputs the amplified output to microcomputer 94. It should be noted that operational amplifier circuit 932 includes an operational amplifier 933, a non-inverting input terminal connected resistor 934, an inverting input terminal connected resistor 934, an inverting input terminal connected resistor 935, a feedback resistor 936, and a capacitor 937.

FIG. 2B shows a well-known internal circuit of microcomputer 94. That is to say, microcomputer 94 generally includes: CPU 94A, the memory unit (ROM (Read Only Memory) 94B and RAM (Random Access Memory) 94C, an Input Port 94E, a PSD 94D (Power Supply Distributor), an Output Port 94F, and a common bus. PSD 94D serves to distribute output voltage Vcc of direct current power supply 280 stably to each unit of microcomputer 94 when power supply is turned on. In addition, the outputs of respective controlled voltages of current adjustment circuits 230 and 240 are started in synchronization with an ON timing of a power supply switch 281, although not shown in the drawings.

Operational amplifier circuit 250 of low-temperature-side gas detecting circuit 91 amplifies a potential difference developed between both output terminals of low-temperature-side terminals of low-temperature-side bridge circuit 210 to output the amplified potential difference to current adjustment circuit 230. In addition, low-temperature-side gas detecting circuit 91 outputs a potential difference VL (corresponds to voltage VL across both ends of lower-temperature heating resistor 211) at the common terminal (electrode film 371) of both of lower-temperature heating resistor 211 of low-temperature-side bridge circuit 210 and fixed resistor 212 to microcomputer 94.

Operational amplifier circuit 260 of high-temperature-side gas detecting circuit 92 outputs the amplified potential difference developed between both output ends of high-temperature-side bridge circuit 220 to current adjustment circuit 240. In addition, high-temperature-side gas detecting circuit 92 outputs the potential difference VH (corresponds to both end terminals VH of higher-temperature heating resistor 221) at the common terminal (electrode film 373) of both of higher-temperature heating resistor 221 and fixed resistor 222 to microcomputer 94.

Amplifier circuit 932 of temperature measuring circuit 93 amplifies the potential difference developed between both output terminals of temperature measuring bridge circuit 220 and outputs the amplified potential difference VT (a value which accords with both terminal voltage VH of temperature measuring resistor 390) to microcomputer 94.

Figure 6:
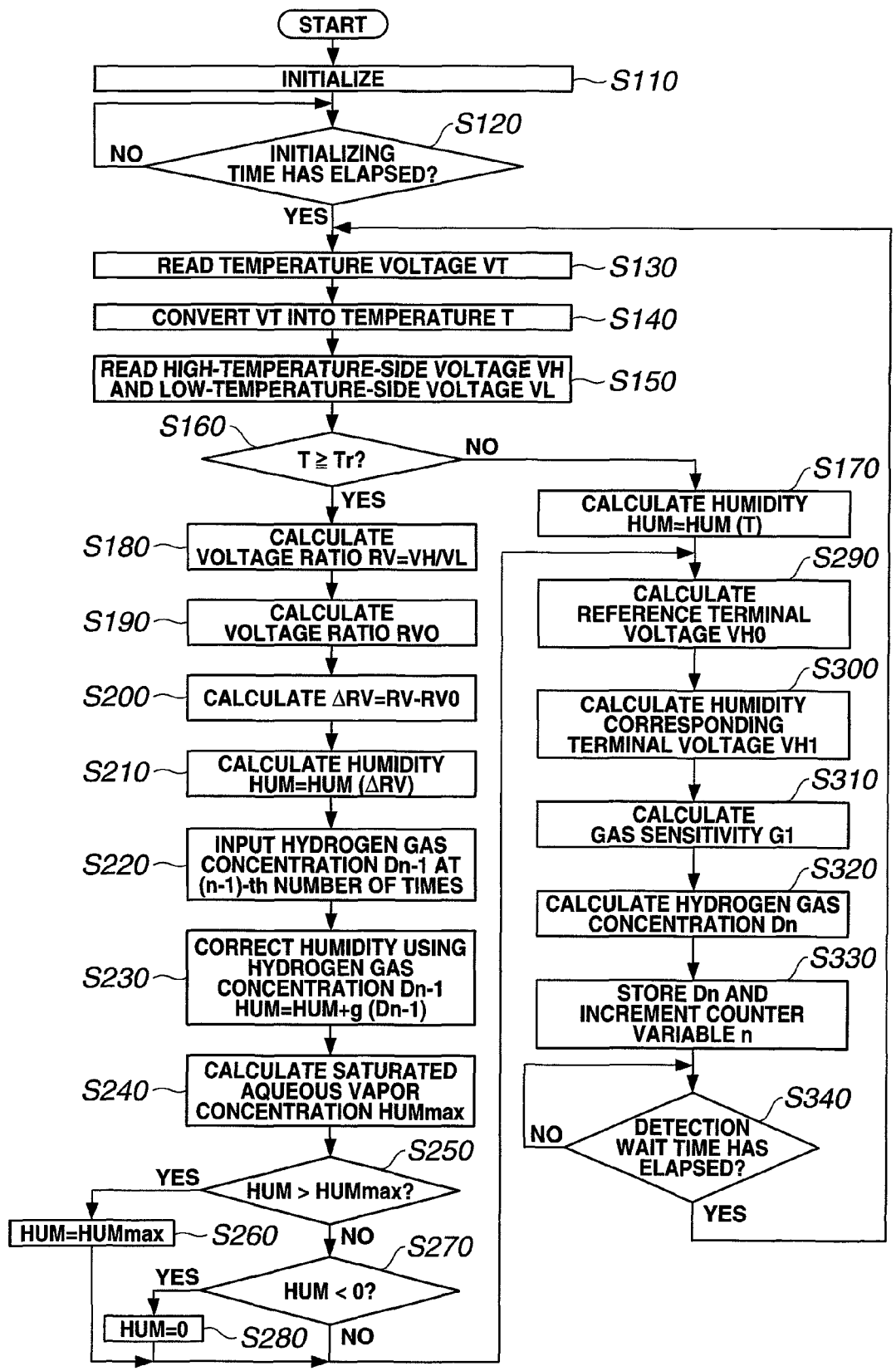
FIG. 6 is a flowchart representing processing contents of a gas detecting procedure of the combustible gas detecting apparatus in the first embodiment shown in FIG. 1.

Microcomputer 94 is operated when the power supply is received from direct current power supply 280 via power supply switch 281. A computer program (a gas detecting procedure) in accordance with a flowchart shown in FIG. 6 is executed. It should be noted that FIG. 6 shows the flowchart representing processing contents of the gas detecting procedure.

In the execution of the gas detecting procedure shown in FIG. 6, microcomputer 94 carries out various processing required for arithmetic operations of hydrogen gas concentration on the basis of the temperature detected by temperature measuring circuit 93 and the output electrical potential differences of low-temperature-side gas detecting circuit 91 and high-temperature-side gas detecting circuit 92. The processing contents of the computer program (gas detecting procedure) are stored in ROM 94B of microcomputer 94 and an arithmetic operation logic unit (CPU 94A) reads the processing contents from ROM 94B during the execution of job (gas detecting procedure).

In the embodiment whose structure has been described above, when combustible gas detecting apparatus 1 is disposed within the atmosphere to be detected, hydrogen gas included in the atmosphere to be detected is caused to flow into flow path forming part 43 of combustible gas detecting apparatus 1. Then, hydrogen gas passes through introducing part 35 of element casing 20 and, thereafter, arrives at gas detection element 60.

In the above-described state, power supply switch 281 is turned on in order for microcomputer 94 to receive the power supply from direct current power supply 280. Thus, microcomputer 94 starts the above-described computer program (the gas detecting procedure) in accordance with the flowchart shown in FIG. 6.

When the gas detecting procedure is activated, at a step S110, microcomputer 94 executes an initialize process (initializing routine). In the initialize process, a software timer activation process and various parameter (variables) in initial value setting processes are executed.

In addition, a time measurement process by means of a software timer incorporated into microcomputer 94 is started. In addition, various parameter (variable) initial setting value procedures are executed so that initial values for internal variables used in the gas detecting procedure are set. For example, the procedure of setting "0" as the initial value to a gas concentration variable D0 which is an initial value from among gas concentration variables Dn (n of Dn denotes a variable of the detected gas concentration representing an integer equal to or larger than zero to store the detected gas concentration and setting a counter variable n of a counter to count the detected number of times to "1" as the initial value (n of the counter variable denotes a natural number (an integer equal to or larger than 1).

At the next procedure of step S120, microcomputer 94 determines whether a predetermined initializing (wait) time has elapsed starting from the activation timing of the gas detecting procedure. In a case where a positive determination is made (Yes at step S120), the routine shown in FIG. 6 goes to a step S130. If a negative determination is made (No at step S120), the step of S110 is repeated to wait for the elapse of time until the positive determination is made at step S120.

it should be noted that the initializing wait time is set to a time duration (required time, for example, 0.5 seconds) required for the temperature of lower-temperature heating resistor 211 to reach to the above-described lower temperature target temperature (150° C.) under the control of current adjustment circuit 230 and required for the higher-temperature heating resistor 221 to reach to the above-described target temperature (330° C.) under the control of current adjustment circuit 240.

If the positive determination (of Yes) at step S120 is made, microcomputer 94 reads amplified potential difference VT outputted from temperature measuring circuit 93 as a temperature voltage VT. It should be noted that temperature voltage VT outputted from temperature measuring circuit 93 indicates a value corresponding to the end voltage across temperature measuring resistor 390 and a value corresponding to temperature T of the atmosphere to be detected.

At the next step S140, microcomputer 94 executes a process of converting temperature voltage VT into temperature T. In details, microcomputer 94 stores in the memory unit (ROM 94B or so forth) conversion data (conversion map data, conversion calculation equations, and so forth) related to a correlation between temperature voltage VT read at step S130 and temperature of the atmosphere to be detected and calculates temperature T corresponding to temperature voltage VT on the basis of the conversion data to obtain a temperature T of the atmosphere to be detected.

At the next step S150, microcomputer 94 reads potential VL outputted from low-temperature-side gas detecting circuit 91 as low-temperature-side voltage VL and executes a read processing of potential VH outputted from high-temperature-side gas detecting circuit 91 as high-temperature-side voltage VH.

At the next step S160, microcomputer 94 compares temperature T converted at step S140 with a predetermined temperature lower limit value Tr to determine whether temperature T is equal to or higher than predetermined temperature lower limit value Tr. If the positive determination is made (Yes) at step S160, the routine goes to a step S180. If the negative determination is made (No at step S160), the routine goes to a step S170. It should be noted that predetermined temperature lower limit value Tr is set to an upper limit value of a temperature range in which a moisture content (a moisture quantity) includable in the atmosphere to be detected is small. In this embodiment, temperature lower limit value Tr is set to 40° C.

If the negative determination (No) is made at step S160 and the routine is transferred to step S170, microcomputer 94 executes a calculate process of calculating humidity HUM of the atmosphere to be detected on the basis of temperature T. In other words, microcomputer 94 stores in the memory unit (ROM 94B and so forth) the conversion data (conversion map data, conversion calculation equation, and so forth) related to the correlation between temperature T of the atmosphere to be detected and humidity HUM of the atmosphere to be detected. Microcomputer 94 calculates humidity HUM corresponding to temperature T calculated at step S140 on the basis of the conversion data to obtain humidity HUM of the atmosphere to be detected.

The calculation equation to calculate humidity HUM based on temperature T can be expressed, for example, as shown in the following equation (1).

$$HUM = a0 \times (T)^2 + b0 \times (T) + c0 \quad (1),$$

wherein a0, b0, and c0 denote predetermined constants. It should be noted that, in the gas detecting procedure of this embodiment, numerical values of humidity HUM are treated as numerical values not a relative humidity but treated as numerical values of an absolute humidity. Then, if the calculate process at step S170 is ended, the routine goes to a step S290.

If the positive determination at step S160 is made (Yes) and the routine goes to step S180, microcomputer 94 executes the calculate process of calculating a detected terminal voltage ratio RV (=VH/VL) of the detected terminal voltages which is a proportion between high-temperature-side voltage VH and low-temperature-side voltage VL.

At the next step S190, microcomputer 94 executes the calculate process of calculating a reference terminal voltage ratio RV0 on the basis of temperature T. It should be noted that reference terminal voltage ratio RV0 (terminal voltage ratio=VH/VL) between high-temperature-side voltage VH and low-temperature-side voltage VL in a case where combustible gas (hydrogen) and moisture are not present in the atmosphere to be detected.

Microcomputer 94 stores in the memory unit (ROM 94B and so forth) the conversion data (the conversion data, the conversion calculation equation, and so forth) related to the correlation between temperature T and reference terminal voltage ratio RV0 and calculates reference terminal voltage ratio RV0 corresponding to temperature T calculated (converted) at step S140 on the basis of the conversion data to obtain reference terminal voltage ratio RV0.

It should be noted that the calculation equation to calculate reference terminal voltage ratio RV0 on the basis of temperature T can, for example, be expressed in the following equation (2).

$$RV0 = a1 \times (T)^2 + b1 \times (T) + c1 \quad (2),$$

wherein a1, b1, and c1 denote predetermined constants.

At the next step S200, microcomputer 94 executes the calculate process of calculating a voltage ratio difference value ΔRV (=RV−RV0) which is a subtraction result of subtracting reference terminal voltage ratio RV0 from detected terminal voltage ratio RV. At the next step S210, microcomputer 94 executes the calculate process of calculating humidity HUM of the atmosphere to be detected on the basis of voltage ratio difference value ΔRV.

Microcomputer 94 stores in the memory unit (ROM 94B and so forth) the conversion data related to the correlation between voltage ratio difference value ΔRV and humidity HUM (conversion map data, conversion calculation equation, and so forth) and calculates humidity HUM corresponding to voltage difference value ΔRV calculated at step S200 on the basis of the conversion data to obtain humidity HUM.

It should be noted that the calculation equation to calculate humidity HUM based on conversion data can be expressed in the following equation (3):

$$HUM = a2 \times (\Delta RV)^2 + b2 \times (\Delta RV) + c2 \quad (3),$$

wherein a2, b2, and c2 denote predetermined constants.

At the next step S220, microcomputer 94 executes a read process of reading hydrogen gas concentration Dn−1 at a time of a (one) previous detection of hydrogen gas concentration in the gas detecting procedure (in details, a numerical value stored in gas concentration variable Dn−1) from the memory unit (RAM 94C and so forth). In other words, microcomputer 94 executes the read out process of reading out hydrogen gas concentration Dn−1 at (n−1)-th number of times at the time of execution at step S220 during the detection at n number of times.

It should be noted that, at the time of a first-time detection (when n=1), hydrogen gas concentration D0 as the previous detection (when n=0) is not present but "0" as the initial value is set to hydrogen gas concentration D0 in the initialize process of step S110 (in details, the numerical value stored in the gas concentration variable D0). Hence, microcomputer 94 executes the read out process of reading this gas concentration variable D0 at the first-time detection. The hydrogen gas concentration Dn (a numerical value stored in gas concentration variable Dn) at a step S330 as will be described later detected during n-th number of time detection is stored in the memory unit (RAM 94C and so forth).

At the next step S230, microcomputer 94 executes a correct process of correcting humidity HUM calculated at step S210 using gas concentration of hydrogen Dn−1 at the previous detection time. In details, at step S230, microcomputer 94 calculates a calculated humidity deviation g(Dn−1) corresponding to hydrogen gas concentration Dn−1 at the previous detection time and corrects humidity HUM by adding calculated humidity deviation g(Dn−1) to humidity HUM calculated at step S210. It should be noted that the calculated humidity deviation described above is a deviation generated due to an influence of the combustible gas concentration (hydrogen gas concentration) on humidity HUM calculated on the basis of voltage ratio difference value ΔRV.

Microcomputer 94 stores in the memory unit (ROM 94B and so forth) the conversion data (the conversion maps date, the conversion calculation equation, and so forth) related to the correlation between the hydrogen gas concentration and calculated humidity deviation g and calculates calculated humidity deviation g corresponding to hydrogen gas concentration Dn−1 at the previous detection time on the basis of the conversion data to obtain calculated humidity deviation g. It should be noted that the conversion date is architected to calculate a value to be added to humidity HUM calculated at step S210 as calculated humidity deviation g(Dn−1) in order to eliminate the detection deviation of the humidity due to the influence of hydrogen gas concentration.

Then, microcomputer 94 substitutes a value of humidity HUM calculated at step S210 to which the value of calculated humidity deviation g(Dn−1) is added into humidity HUM to execute the correction process of humidity HUM. It should be noted that a calculation equation to calculate calculated humidity deviation g on the basis of hydrogen gas concentration Dn−1 during the previous detection can, for example, be expressed in the following equation (4).

$$g = m \times (Dn-1) \quad (4),$$

wherein m denotes a predetermined constant.

In addition, the calculation equation to correct humidity HUM (ΔRV) calculated at step S210 on the basis of hydrogen concentration Dn−1 at the time of the previous detection can, for example, be expressed in the following equation (5).

$$HUM = HUM(\Delta RV) + g \quad (5)$$
$$= HUM(\Delta RV) + m \times (Dn-1).$$

At the next step S240, microcomputer 94 executes the calculate process of calculating a saturated aqueous vapor concentration HUMmax in the atmosphere to be detected on the basis of temperature T. It should be noted that saturated aqueous vapor concentration HUMmax is a value corresponding to a maximum value of a feasible humidity range of an actual atmosphere to be detected.

Microcomputer 94 stores in the memory unit (ROM 94B and so forth) the conversion date (a conversion map data, a conversion calculation equation, and so forth) related to the correlation between temperature T and saturated aqueous vapor concentration HUMmax and calculates saturated aqueous vapor concentration HUMmax corresponding to temperature T calculated at step S140 on the basis of the conversion data to obtain saturated aqueous vapor concentration HUMmax.

It should be noted that the calculation equation to calculate saturated aqueous vapor concentration HUMmax on the basis of temperature T can, for example, be expressed in the following equation (6).

$$HUMmax = a3 \times (T)^2 + b3 \times (T) + c3 \quad (6),$$

wherein a3, b3, and c3 denote predetermined constants.

At the next step S250, microcomputer 94 executes a compare process to compare corrected humidity HUM by the correction of correct process at step S230 with saturated aqueous vapor concentration HUMmax calculated at step S240 to determine whether corrected humidity HUM is larger than saturated aqueous vapor concentration HUMmax. If HUM>HUMmax (Yes) at step S250, the routine goes to a step S260. If HUM≦HUMmax (No) at step S250, the routine goes to a step S270.

If the positive determination is made at step S250 and the routine is transferred to step S260, microcomputer 94 substitutes saturated aqueous vapor concentration HUMmax into humidity HUM. In other words, at step S260, microcomputer 94 executes the further correct process of further correcting humidity HUM corrected at step S230. Specifically, microcomputer 94 sets saturated aqueous vapor concentration HUMmax as corrected humidity HUM.

If the negative determination (No) is made at step S250 and the routine is transferred to step S270, microcomputer 94 determines whether corrected humidity HUM by the correct process at step S230 is smaller than zero (0), If the positive determination (Yes) is made at step S270, the routine goes to a step S280. If the negative determination (No) is made at step S270, the routine goes to a step S290.

If the positive determination is made at step S270 and the routine is transferred to step S280, microcomputer 94 substitutes 0 into humidity HUM. In other words, microcomputer 94, at step S280, executes the further correct process of correcting further humidity HUM corrected at step S230. Specifically, microcomputer 94 sets zero to corrected humidity HUM.

If any one of the processes at steps S170, S260, and S280 is ended or the negative determination (No) is made at step S270, the routine goes to step S290. At step S290, microcomputer 94 executes the calculate process of calculating a reference terminal voltage VH0 on the basis of temperature T. It should be noted that reference terminal voltage VH0 indicates high-temperature-side voltage VH (the voltage across both end of higher-temperature heating resistor 221) in a case where the combustible gas (hydrogen) and moisture are not present in the atmosphere to be detected.

Then, microcomputer 94 stores in the memory unit (ROM 94B and so forth) the conversion data (the conversion map data, the conversion calculation equation, and so forth) related to the correlation between temperature T and reference terminal voltage VH0 and calculates reference terminal voltage VH0 corresponding to temperature T calculated at step S140 on the basis of the conversion data to obtain reference terminal voltage VH0.

It should be noted that the calculation equation to calculate reference terminal voltage VH0 on the basis of temperature T can be, for example, expressed in the following equation (7):

$$VH0 = a4 \times (T)^2 + b4 \times (T) + c4 \tag{7}$$

wherein a4, b4, and c4 denote predetermined constants.

At the next step S300, microcomputer 94 executes the calculate process of calculating a humidity corresponding terminal voltage VH1 on the basis of humidity HUM and reference terminal voltage VH0. It should be noted that humidity corresponding terminal voltage VH1 is the high-temperature-side voltage VH (terminal voltage VH of higher-temperature heating resistor 221) in a case where the combustible gas is not present in the atmosphere to be detected but only aqueous vapor is present in the atmosphere to be detected.

Microcomputer 94 stores in the memory unit (ROM 94B and so forth) the conversion data (the conversion map data, the conversion calculation equation, and so forth) related to the correlation among humidity HUM, reference terminal voltage VH0, and humidity corresponding terminal voltage VH1 and calculates humidity corresponding terminal voltage VH1 corresponding to humidity HUM and reference terminal voltage VH0 calculated at step S290 on the basis of the conversion data to obtain humidity corresponding terminal voltage VH1. It should be noted that the calculation equation to calculate humidity corresponding terminal voltage VH1 on the basis of humidity HUM and reference terminal voltage VH0 can, for example, be expressed in the following equation (8).

$$VH1 = a5 \times (HUM)^2 + b5 \times (HUM) + VH0 \tag{8}$$

wherein a5 and b5 denote predetermined constants.

At the next step S310, microcomputer 94 executes the calculate process of calculating a gas sensitivity G1 on the basis of temperature T. It should be noted that gas sensitivity G1 is a numerical value used in the calculation of the hydrogen gas concentration on the basis of a difference value (a high-temperature-side voltage difference value $\Delta VH$ (=VH–VH1)) between high-temperature-side voltage VH and humidity corresponding terminal voltage VH1. It should also be noted that gas sensitivity G1 is the numerical value determined according to kinds (a material quality, a shape, or so forth) of heating resistors (left-side heating resistor 331 and right-side heating resistor 332).

Then, microcomputer 94 stores in the memory unit (ROM 94B and so forth) the conversion data related to the correlation between temperature T and gas sensitivity G1 (the conversion map data, the conversion calculation equation, and so forth) and calculates gas sensitivity G1 corresponding to temperature T to obtain gas sensitivity G1. The calculation equation to calculate gas sensitivity G1 on the basis of temperature T can, for example, be represented in the following equation 9.

$$G1 = a6 \times (T)^2 + b6 \times (T) + c6 \tag{9}$$

wherein a6, b6, and c6 denote respective predetermined constants.

At the next step S320, microcomputer 94 executes the calculate process of calculating hydrogen gas concentration Dn on the basis of high-temperature-side voltage difference value $\Delta VH$ (=VH–VH1) and gas sensitivity G1. It should be noted that hydrogen gas concentration Dn is obtained by dividing high-temperature-side voltage difference value $\Delta VH$ by gas sensitivity G1.

The calculation equation to calculate hydrogen concentration Dn on the basis of high-temperature-side voltage difference value $\Delta VH$ and gas sensitivity G1 can, for example, be expressed in the following equation (10).

$$Dn = \Delta VH/G1 \tag{10}$$

At the next step S330, microcomputer 94 stores in the memory unit (RAM 94C and so forth) hydrogen gas concentration Dn calculated at step S320 and executes the process of incrementing counter variable n by one (addition of one).

At the next step S340, microcomputer 94 determines whether a predetermined detection wait time has elapsed from a time at which the positive determination at step S120 is made or from a time at which the positive determination at step S340 at the previous detection time has been made. If the predetermined detection wait time has elapsed (Yes) at step S340, the routine goes to step S130. If the predetermined detection wait time has not elapsed (No) at step S340, microcomputer 94 waits until the positive determination is made at step S340. It should be noted that the detection wait time is preset according to the detection period of the hydrogen gas concentration and is preset to a time duration (for example, 10 milliseconds [ms]) such that the subsequent detection timing comes within the time duration within which the hydrogen gas concentration is remarkably varied.

If the positive determination is made at step S340, the routine again goes to step S130. Then, since the processes from step S130 to step S340 are repeatedly executed, the hydrogen gas concentration is repeatedly detected. It should be noted that, in this embodiment, left-side heating resistor 331 and right-side heating resistor 332 correspond to first and second heating resistors described in claims, current adjustment circuit 230 and operational amplifier circuit 260 correspond to a power supply control section (means) described therein, and temperature measuring circuit 93 including temperature measuring resistor 390 and microcomputer 94 executing steps of S130 and S140 correspond to a temperature detecting section (means) described therein.

In addition, microcomputer 94 executing step S150 corresponds to a voltage detecting section described therein, microcomputer 94 executing the processes from step S180 to step S210 corresponds to a humidity calculating section (means) described therein, and microcomputer 94 executing the processes from step S290 to step S320 correspond to a concentration calculating section (means) described therein.

Furthermore, the memory unit (RAM 94C and so forth) of microcomputer 94 storing hydrogen gas concentration Dn corresponds to a gas concentration storing section (means) described therein, microcomputer 94 executing steps S220 and S230 correspond to a humidity correcting section (means) described therein, microcomputer 94 executing the process at step S160 corresponds to a temperature determining section (means) described therein, microcomputer 94 executing the process of step S170 corresponds to a temperature corresponding humidity calculating section (means), and higher-temperature heating resistor 221 (right-side heating resistor 332) corresponds to heating resistor (a high-temperature-side resistance element) for which the power supply is controlled to correspond to higher-temperature heating resistor.

In addition, microcomputer 94 executing the process at step S180 corresponds to a voltage ratio calculating section (means), microcomputer 94 executing the process at step S190 corresponds to a reference terminal voltage ratio calculating section (means), and microcomputer 94 executing the process at step S210 corresponds to a voltage ratio difference value corresponding humidity calculating section (means).

Furthermore, silicon made semiconductor substrate 310 corresponds to a semiconductor substrate, upper insulating layer 323 and lower insulating layer 324 correspond to an insulating layer, heating resistors 330 (left-side heating resistor 331 and right-side heating resistor 332) correspond to a substrate heating resistor, and inner protective layer 350 and outer protective layer 360 correspond to a protective layer.

In addition, microcomputer 93 executing the process of step S240 correspond to a saturated aqueous vapor concentration calculating section (means), microcomputer 94 executing the process of step S260 corresponds to a humidity upper limit value setting section (means), and microcomputer 94 executing the process of step S280 corresponds to a humidity lower limit value setting section (means).

As described above, combustible gas detecting apparatus 1 in this embodiment calculates hydrogen gas concentration Dn using humidity HUM (S230) corrected using hydrogen gas concentration Dn−1 at the previous detection time without a direct use of humidity HUM calculated at step S210.

In detail, microcomputer 94 calculates (step S300) calculates humidity corresponding terminal voltage VH1 using humidity HUM corrected at step S230, calculates a difference value (high-temperature-side voltage difference value ΔVH), calculates high-temperature-side voltage difference value ΔVH between high-temperature-side voltage VH and humidity corresponding terminal voltage VH1, and calculates (step S320) hydrogen gas concentration Dn on the basis of high-temperature-side voltage difference value ΔVH and gas sensitivity G1.

Therefore, even in a case where the hydrogen gas concentration in the atmosphere to be detected in which combustible gas detecting apparatus 1 is installed is varied and the deviation occurs in the result of calculation of humidity HUM at step S210 due to the variation in the concentration, humidity HUM after the correction made at step S230 is a value on which an influence of the hydrogen gas concentration is reflected. In other words, humidity HUM after the correction made at step S230 provides the value approximate to an actual humidity as compared with humidity HUM calculated at step S210 and the deviation to the actual humidity provides a minor value.

Therefore, combustible gas detecting apparatus 1 calculates hydrogen gas concentration Dn using humidity HUM after the correction (corrected humidity HUM) which is a minor deviation and can detect the hydrogen gas concentration while suppressing the detection deviation of the humidity due to the variation in the hydrogen gas concentration.

Consequently, even if, according to combustible gas detecting apparatus 1 of this embodiment, the hydrogen gas concentration is varied, the detection deviation of the humidity is difficult to occur and a reduction of a detection accuracy of hydrogen gas can be suppressed.

In addition, in the gas detecting procedure of this embodiment, microcomputer 94 executes the storing process in which the gas concentration is stored at step S330 whenever the gas concentration is calculated at step S320. Therefore, hydrogen gas concentration Dn−1 used for the correction process (step S230) provides a newest hydrogen gas concentration from among a plurality of hydrogen gas concentrations detected in the past.

As described above, combustible gas detecting apparatus 1 in the embodiment according to the present invention is architected to correct humidity HUM always using the newest hydrogen gas concentration and can correct humidity HUM on the basis of value (Dn−1) approximate to the (actual) hydrogen gas concentration in the atmosphere to be detected at the time of the hydrogen gas concentration detection.

Hence, according to combustible gas detecting apparatus 1 in this embodiment, humidity HUM can be corrected on the basis of the value approximate to the (actual) gas concentration in the atmosphere to be detected at the time of the gas concentration detection. Consequently, a correction accuracy in the humidity correction can be improved and the reduction in detection accuracy of the hydrogen gas concentration can be suppressed.

In addition, in combustible gas detecting apparatus 1, gas detection element 60 having inner protective layer 350 and outer protective layer 360 enclosing the first and second heating resistors (left-side heating resistor 331 and right-side heating resistor 332) are provided. Hence, even if harmful substances which erode heating resistors (left-side heating resistor 331 and right-side heating resistor 332) are present in the atmosphere to be detected, hydrogen gas can be detected while suppressing erosions of the heating resistors.

In addition, in combustible gas detecting apparatus 1 in this embodiment, the target temperature of lower-temperature heating resistor 211 (left-side heating resistor 331) is 150° C. and the target temperature of higher-temperature heating resistor 221 (right-side heating resistor 332) is 330° C. That is to say, both of the target temperatures of lower-temperature heating resistor 211 (left-side heating resistor 331) and higher-temperature heating resistor 221 (right-side heating resistor) are set within a range from 150° C. to 500° C.

As described above, the temperature range of target temperature is set so that the temperatures of both lower-temperature heating resistor 211 (left-side heating resistor 331) and higher-temperature heating resistor 221 (right-side heating resistor) can be controlled to be above a temperature range (150° C. or higher) exceeding assuredly a boiling point of water under the atmosphere (the atmospheric pressure) and can detect hydrogen gas even if the atmosphere to be detected is under a high-humidity environment including the dew point. As described above, the temperature range of the target temperatures is set so that both temperatures of lower-temperature heating resistor 211 (left-side heating resistor 331) and higher-temperature heating resistor 221 (right-side heating resistor 332) can be set to a temperature range lower than an ignition (or an explosion) temperature of hydrogen gas (500° C. or lower). Thus, temperatures of lower-temperature heating resistor 211 (left-side heating resistor 331) and higher-temperature heating resistor 221 (left-side heating resistor 331) can be suppressed from being raised to the ignition temperature (or explosion temperature) of hydrogen gas and the ignition of hydrogen gas can be prevented.

In addition, in combustible gas detecting apparatus 1, the target temperature of lower-temperature heating resistor 211 (left-side heating resistor 331) is 150° C. and the target temperature of higher-temperature heating resistor 221 (right-side heating resistor 332) is 330° C. That is to say, a difference between the target temperature of lower-temperature heating resistor 211 (left-side heating resistor 331) and that of higher-temperature heating resistor 221 (right-side heating resistor 332) is set to 50° C. or higher.

It should be noted that, as the difference between the target temperature of lower-temperature heating resistor 211 (left-side heating resistor 331) and that of higher-temperature heating resistor 221 (right-side heating resistor 332) becomes larger, the detection accuracy when the humidity of the atmosphere to be detected becomes more remarkably be improved.

Consequently, if, in combustible gas detecting apparatus 1, microcomputer 94 determines, at the determination process of step S250, that the value of humidity HUM after the correction (corrected humidity HUM) is larger than saturated aqueous vapor concentration HUMmax (the positive determination is made), microcomputer 94 executes the process of substituting saturated aqueous vapor concentration HUMmax into humidity HUM. Furthermore, if, in combustible gas detecting apparatus 1, at the determination process of step S270, in a case where the value of corrected humidity HUM (after the correction is made) is smaller than 0 (the positive determination is made), microcomputer 94 executes the process of setting 0 as corrected humidity HUM.

As described above, in a case where corrected humidity HUM at step S230 is set to an inappropriate value, microcomputer 94 executes the process of further correcting corrected humidity HUM so that humidity HUM used for the calculation of hydrogen gas concentration can be prevented from being set to the infeasible (unrealizable) humidity range of the actual atmosphere to be detected and the reduction of the detection accuracy in the hydrogen gas concentration can be suppressed.

Measurement results evaluating what values corrected humidity HUM and hydrogen gas concentration Dn are indicated when the hydrogen gas concentration is modified under the condition that the humidity of the atmosphere to be detected is made constant will, hereinbelow, be explained.

It should be noted that, in a case where, in these measurements, while the humidity of the atmosphere to be detected was maintained constant at 0 vol % (0 [vol %]), the hydrogen gas concentration in the atmosphere to be detected was modified in five stages (0→1→2→3→4→0 vol % [vol %]), corrected humidity HUM and hydrogen gas concentration Dn calculated in combustible gas detecting apparatus 1 were measured.

In addition, as a comparative example, the humidity and the hydrogen gas concentration in a previously proposed combustible gas detecting apparatus 1 for which the correction for the humidity is not carried out were measured. It should be noted that, in the previously proposed combustible gas detecting apparatus, humidity HUM in the same process as step S210 in this embodiment is calculated, the difference value (higher-temperature-side voltage difference value ΔVH) between humidity corresponding terminal voltage VH1 and humidity corresponding terminal voltage VH1 is calculated, and hydrogen gas concentration Dn is calculated on the basis of higher-temperature-side difference value ΔVH and gas sensitivity G1 (the same process as step S320).

Figure 7:
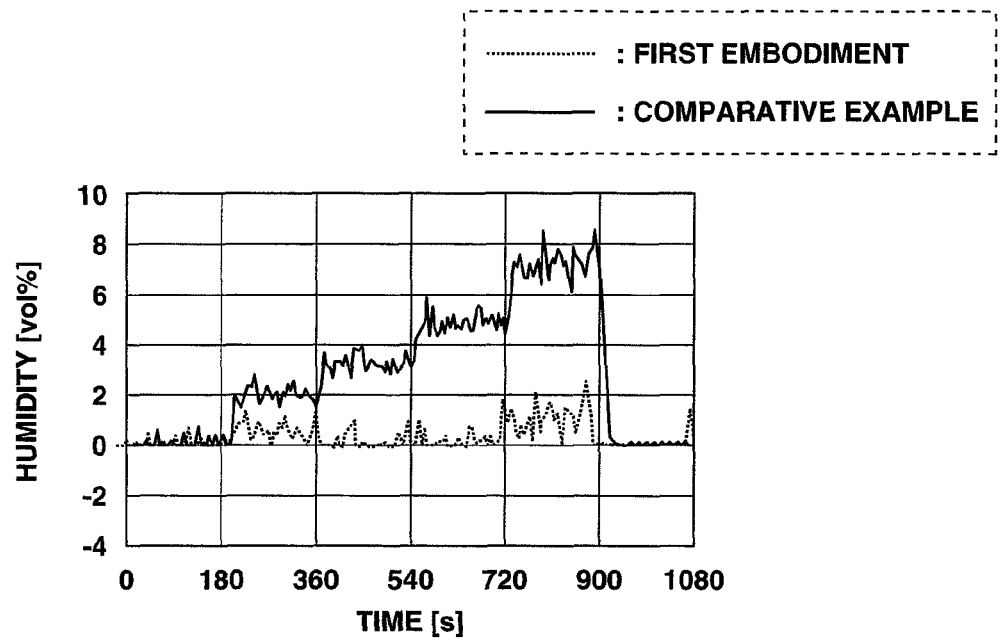
FIG. 7 is an explanatory graph representing measurement results of humidity in the first embodiment and in a comparative example.
Figure 8:
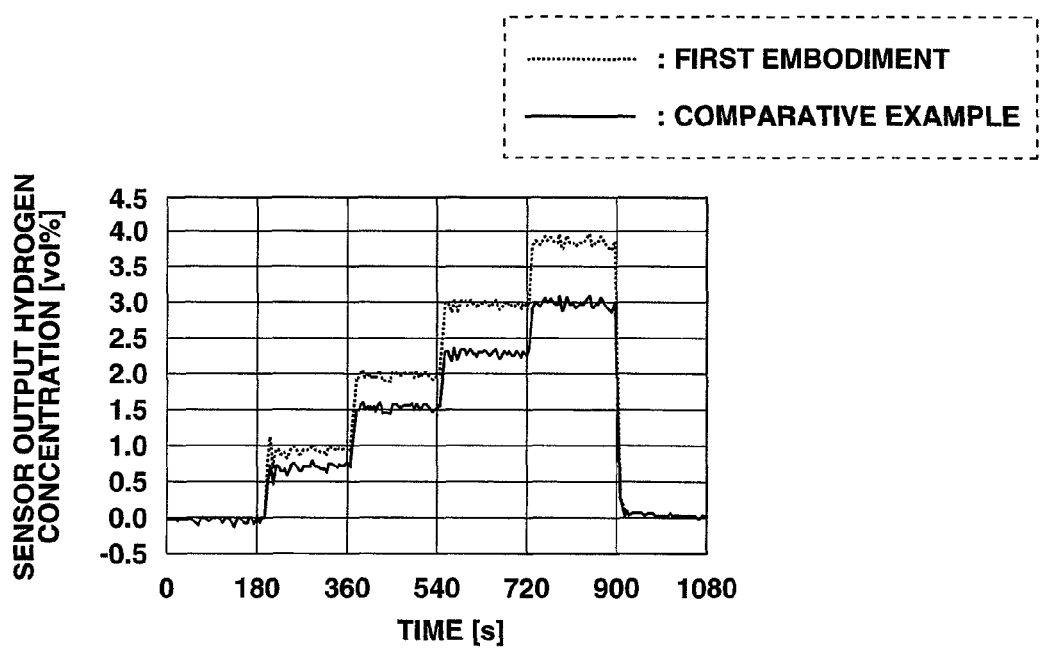
FIG. 8 is an explanatory view representing a result of measurements of hydrogen (gas) concentration in the first embodiment and in the comparative example.

FIG. 7 shows the results of measurements of humidity and FIG. 8 shows the results of measurements of hydrogen gas concentration. It should be noted that dot lines in FIGS. 7 and 8 denote measurement results in the this embodiment and solid lines in FIGS. 7 and 8 denote measurement results in the comparative example (viz., the previously proposed combustible gas detecting apparatus).

First, according to the measurement result of the humidity shown in FIG. 7, it is appreciated that the humidity of the calculation result in accordance with the variation in the hydrogen gas concentration was varied in spite of the fact that the humidity of the atmosphere to be detected (in other words, the actual humidity) was constant. On the other hand, in this embodiment, it is appreciated that humidity HUM was not largely varied at a timing at which the hydrogen gas concentration is switched to the remaining one of the five stages and humidity HUM as the calculation result did not receive the influence of the hydrogen gas concentration.

Next, according to the measurement results of hydrogen gas concentration shown in FIG. 8 in the case of the comparative example (the previously proposed combustible gas detecting apparatus), it is possible to judge that the hydrogen gas concentration is varied from the fact that the hydrogen gas concentration which is the result of calculation is varied when the hydrogen gas concentration in the atmosphere to be detected (in other words, the actual hydrogen gas concentration) is varied whenever 180 seconds have elapsed. However, the hydrogen gas concentration as the result of calculation indicates a value different from the actual hydrogen gas concentration. Hence, it is difficult to detect accurately the hydrogen gas concentration in the comparative example (the previously proposed combustible gas detecting apparatus). For example, when the actual hydrogen gas concentration is 4.0 vol %, the measurement result of the hydrogen gas concentration in the comparative example (the previously proposed combustible gas detecting apparatus) is 3.0 vol %. It is, hence, appreciated that the deviation occurs in the detected value of the hydrogen gas concentration.

On the other hand, it is appreciated that, in this embodiment, when the actual hydrogen gas concentration is varied, the hydrogen gas concentration which is the result of calculation is varied and the hydrogen gas concentration as the result of calculation indicates the same numerical value as the actual hydrogen gas concentration.

Hence, it is appreciated that, according to this result of measurement, in combustible gas detecting apparatus 1 in this embodiment, the detection deviation of the humidity is difficult to occur even if the hydrogen gas concentration is varied and the reduction in the detection accuracy of hydrogen gas can be suppressed.

It should be noted that, in the above-described embodiment (first embodiment), the combustible gas detecting apparatus architected to detect the combustible gas concentration (hydrogen gas concentration) using terminal voltage VH of right-side heating resistor 332 which is higher-temperature heating resistor 221 from among the detecting elements of first and second heating resistors (left-side heating resistor 331 and right-side heating resistor 332) has been explained. In other words, in the combustible gas detecting apparatus in the first embodiment, the terminal voltage used to detect combustible gas is only "the terminal voltage across the high-temperature-side resistance element".

However, the terminal voltage used to detect the combustible gas is not limited to only the terminal voltage across the high-temperature-side resistance element (heating resistor) but it is, for example, possible to be the difference value (voltage difference) between the terminal voltage across the high-temperature-side resistance element and the terminal voltage across the low-temperature-side resistance element.

As a second preferred embodiment of combustible gas detecting apparatus according to the present invention, a second combustible gas detecting apparatus architected to detect combustible gas (hydrogen gas) using "the difference value (voltage difference) between the terminal voltage across the high-temperature-side resistance element and the terminal voltage across the low-temperature-side resistance element" will be described below.

It should be noted that the second combustible gas detecting apparatus in the second embodiment has many common features to combustible gas detecting apparatus 1 in the first embodiment and a part of processing contents in the gas detecting procedure is different. Hence, the second combustible gas detecting apparatus will be described mainly with the different part as center.

First, second combustible gas detecting apparatus includes element casing 20, housing 40, and gas detection element 60 in the same way as combustible gas detecting apparatus 1 in the first embodiment and is used, for example, in the fuel cell system for detecting hydrogen gas leaked from the fuel cell in the fuel cell system. Since the structures of element casing 20, housing 40, and gas detection element 60 in the second combustible gas detecting apparatus are the same as those described in the first embodiment, the descriptions thereof will herein be omitted. Microcomputer 94 in the second combustible gas detecting apparatus is mounted on circuit board 41 in the internal of housing 40 in the same way as that in combustible gas detecting apparatus 1 in the first embodiment (as shown in FIG. 1). Control circuit 200 in the second combustible gas detecting apparatus, as shown in FIG. 2A, includes: low-temperature-side gas detecting circuit 91; high-temperature-side gas detecting circuit 92; and temperature measuring circuit 93. The second combustible gas detecting apparatus includes: microcomputer 94; direct current (DC) power supply 280; and power supply switch 281.

It should be noted that the hardware structure of control circuit 200 in the second combustible gas detecting apparatus is the same as that in the first embodiment and, therefore, the description thereof will herein be omitted. In the second embodiment, when housing 40 of the second combustible gas detecting apparatus is disposed within the atmosphere to be detected, hydrogen gas included in the atmosphere to be detected is caused to flow into flow path forming part 43 of housing 40. Thereafter, hydrogen gas is passed through introducing part 35 of element casing 20 into space to be detected 39 and, thereafter, arrives at gas detection element 60.

Figure 9:
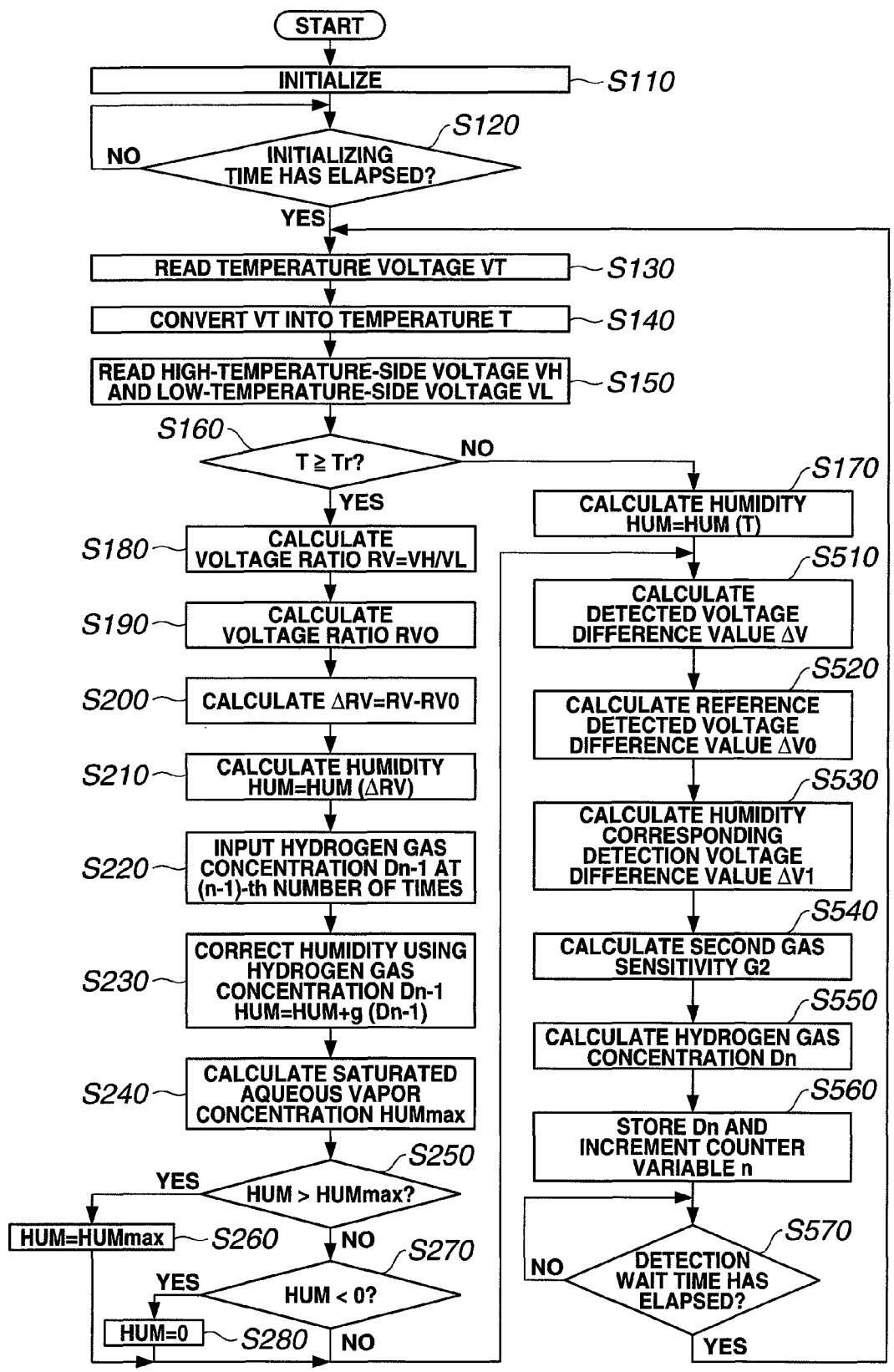
FIG. 9 is a flowchart representing processing contents of the gas detecting procedure of the combustible gas detecting apparatus in a second preferred embodiment according to the present invention.

In such a state as described above, power supply switch 281 is turned on so that microcomputer 94 receives the direct current (DC) power supply from direct current (DC) power supply 280. At this time, microcomputer 94 starts the execution of the computer program (a second gas detecting procedure) in accordance with a flowchart shown in FIG. 9. FIG. 9 shows the flowchart representing the processing contents of a second gas detecting procedure.

In the processing contents of the second gas detecting procedure shown in FIG. 9, the processing contents of steps S110 to S280 are the same as the gas detecting procedure in the first embodiment shown in FIG. 6. The descriptions of the same steps of S110 to S280 will herein be omitted. In the second gas detecting procedure shown in FIG. 9, if any one of the processes at step S170, S260, and S280 is ended or the negative determination (NO) at step S270 is made, the routine goes to a step S510.

At step S510, microcomputer 94 executes the process of calculating a detected voltage difference value $\Delta V$ (=VH−VL) which is a difference value between high-temperature-side voltage VH and low-temperature-side voltage VL using high-temperature-side voltage VH and low-temperature-side voltage VL.

At the next step S520, microcomputer 94 executes the process of calculating a reference detected voltage difference value $\Delta V0$ on the basis of temperature T. It should be noted that reference detected voltage difference value $\Delta V0$ is detected voltage difference value $\Delta V$ (=VH−VL) in a case where combustible gas (hydrogen) and moisture are absent (not present) in the atmosphere to be detected.

Microcomputer 94 stores in the memory unit (ROM 94B and so forth) the conversion data (the conversion map data, the conversion calculation equation, and so forth) related to the correlation between temperature T and reference detected voltage difference value $\Delta V0$. Reference detected voltage difference value $\Delta V0$ is obtained by calculating reference detected voltage difference value $\Delta V0$ corresponding to temperature T calculated at step S140 on the basis of the conversion data.

It should be noted that the calculation equation to calculate reference detected voltage difference value $\Delta V0$ on the basis of temperature T can, for example, be expressed in the following equation (11).

$$\Delta V0 = a7 \times (T)^2 + b7 \times (T) + c7 \qquad (11),$$

wherein a7, b7, and c7 denote predetermined constants.

At the next step 530, microcomputer 94 executes the process of calculating a humidity corresponding voltage difference value $\Delta V1$ on the basis of humidity HUM and reference detected voltage difference value $\Delta V0$. It should be noted that humidity corresponding detected difference value $\Delta V1$ is a detected voltage difference value $\Delta V$ (=VH−VL) at temperature T in a case where the combustible gas (hydrogen) is not present (absent) in the atmosphere to be detected.

Microcomputer 94 stores in the memory unit (ROM 94B and so forth) the conversion data (the conversion map data, the conversion calculation equation, and so forth) related to the correlation among humidity HUM, reference detected voltage difference value $\Delta V0$, and humidity corresponding detected voltage difference value $\Delta V1$ and calculates humidity HUM and humidity corresponding detected voltage difference value $\Delta V1$ corresponding to reference detected voltage difference value $\Delta V0$ on the basis of the conversion data to obtain humidity corresponding detected voltage difference value $\Delta V1$.

It should be noted that the calculation equation to calculate humidity corresponding detected voltage difference value $\Delta V1$ on the basis of humidity HUM and reference detected voltage difference value $\Delta V0$ can, for example, be expressed in the following equation (12).

$$\Delta V1 = a8 \times (HUM)^2 + b8 \times (HUM) + \Delta V0 \qquad (12),$$

wherein a8 and b8 denote predetermined constants.

At the next step S540, microcomputer 94 executes the process of calculating a second gas sensitivity G2 on the basis of temperature T. It should be noted that second gas sensitivity G2 is a numerical value used for calculating hydrogen gas concentration Dn on the basis of the difference value (concentration detecting difference value $\Delta VA$) between detected voltage difference value $\Delta V$ (=VH−VL) and humidity corresponding detected voltage difference value $\Delta V1$. In addition, second gas sensitivity G2 is a numerical value determined according to kinds (material quality, shape, and so forth) of heating resistors 330 (left-side heating resistor 331 and right-side heating resistor 332) and temperature T to obtain second gas sensitivity G2.

The calculation equation to calculate second gas sensitivity G2 on the basis of temperature T can, for example, be expressed in the following equation (13).

$$G2 = a9 \times (T)^2 + b9 \times (T) + c9 \qquad (13),$$

wherein a9, b9, and c9 denote predetermined constants.

At the next step S550, microcomputer 94 executes the calculate process of calculating hydrogen gas concentration Dn on the basis of concentration detecting difference value $\Delta VA$ and second gas sensitivity G2. It should be noted that hydrogen gas concentration Dn is obtained by dividing concentration detecting difference value $\Delta VA$ by second gas sensitivity G2.

The calculation equation to calculate hydrogen gas concentration Dn on the basis of concentration detecting difference value ΔVA and second gas sensitivity G2 can, for example, be expressed in the following equation (14).

$$Dn=\Delta VA/G2 \quad (14).$$

At the next step S560, microcomputer 94 executes the store process of storing hydrogen gas concentration Dn calculated at step S550 in the memory unit (RAM 94C and so forth) and an increment process of adding one to counter variable n (increment process for counter variable n).

At the next step S570, microcomputer 94 determines whether a predetermined detection wait time has elapsed staring from a time at which the positive determination (Yes) at step S120 is made or from a time at which the positive determination (Yes) during the previous second gas detecting procedure shown in FIG. 9 is made at step S570.

It should be noted that the above-described detection wait time is predetermined according to a detection period of hydrogen gas concentration and is preset to a time (for example, 10 milliseconds) such that the subsequent detection period comes within a time during which the hydrogen gas concentration is not remarkably varied.

If the positive determination at step S570 is made at step S570 (Yes), the routine is again transferred to step S130. Then the series of processes from step S130 to step S280 and from step S130 to step S570 are repeatedly executed to repeatedly detect the hydrogen gas concentration.

As described above, in the second combustible gas detecting apparatus in the second embodiment, hydrogen gas concentration Dn is calculated using humidity HUM (step S230) corrected using the previously detected hydrogen gas concentration Dn−1 without direct use of humidity HUM calculated at step S210 when hydrogen gas concentration Dn is calculated in the same way as the first embodiment described above.

In details, humidity corresponding detected voltage difference value ΔV1 using humidity HUM corrected at step S230 is calculated (at step S530), the difference value (concentration detecting difference value ΔVA (ΔVA=ΔV−ΔV1)) between detected voltage difference value ΔV and humidity corresponding detected voltage difference value ΔV1 is calculated, and hydrogen gas concentration Dn on the basis of concentration detecting difference value ΔVA and second gas sensitivity G2 is calculated (at step S550).

Therefore, even if the hydrogen gas concentration in the atmosphere to be detected in which the second combustible gas detecting apparatus is installed is varied and the deviation in the result of calculation of humidity HUM at step S210 occurs due to the variation in the hydrogen gas concentration, corrected humidity HUM corrected at step S230 provides a value on which the variation in the hydrogen gas concentration is reflected. In other words, corrected humidity HUM after the correction made at step S230 becomes a value approximate to the actual humidity and provides a value which has a small deviation to the actual humidity, as compared with humidity HUM calculated at step S210.

From the above-described point, second combustible gas detecting apparatus in the second embodiment is difficult to generate the detection deviation of the humidity even if the hydrogen gas concentration is varied in the same way as the first embodiment and can suppress the reduction in the detection accuracy of hydrogen gas.

In the second gas detecting procedure in the second embodiment, microcomputer 94 executes the store process of storing the gas concentration at step S560 whenever the gas concentration is calculated at step S550. Hence, hydrogen gas concentration Dn−1 used in the subsequent correction process (at step S230) provides the newest hydrogen gas concentration from among the plurality of hydrogen gas concentrations detected in the past.

Since the second combustible gas detecting apparatus is architected to carry out the correction of humidity HUM always using the newest hydrogen gas concentration, humidity HUM can be corrected on the basis of the value Dn−1 approximate to the hydrogen gas concentration in the atmosphere to be detected during the gas concentration detection process.

Since, according to the combustible gas detecting apparatus in the second embodiment, humidity HUM can be corrected on the basis of the value approximate to the gas concentration in the atmosphere to be detected at the time of the gas concentration detection. The correction accuracy in the humidity correction can be improved and a reduction in the detection accuracy of hydrogen gas concentration can be suppressed.

It should be noted that, in the combustible gas detecting apparatus in the second embodiment, microcomputer 94 executing the processes from steps S510 to S550 corresponds to the concentration calculating section described in the claims.

As described hereinabove, the preferred embodiments according to the present invention have been described. The present invention is not limited to the embodiments described above but various modifications can be made. For example, in the first and second embodiments described above, the embodiment in which the terminal voltage used to detect the combustible gas is only the terminal voltage across the high-temperature-side resistance element and the other embodiment in which the terminal voltage used to detect the combustible gas is the difference value (voltage difference) between the terminal voltage across the high-temperature-side resistance element (higher-temperature heating resistor) and the terminal voltage across the low-temperature-side resistance element (lower-temperature heating resistor) have been described.

However, the terminal voltage used to detect the combustible gas is not limited to the above-described forms. As another embodiment, for example, the terminal voltage used to detect the combustible gas may be a ratio (a voltage ratio) between the terminal voltage across high-temperature-side resistance element (higher-temperature heating resistor) and the terminal voltage across low-temperature-side resistance element (lower-temperature-heating resistor).

In addition, in the above-described embodiments, the memory unit (RAM 94C and so forth) of microcomputer 94 (storing the combustible gas concentration therein) stores a plurality of hydrogen gas concentrations Dn and stores a plurality of combustible gas concentrations which provide a past history. The memory unit storing the combustible gas concentration may be structured to store only a single combustible gas concentration. In other words, the combustible gas concentration used to correct humidity HUM is only the combustible gas concentration during one previous gas time. Hence, the plurality of combustible gas concentrations are not always needed. Hence, the memory unit (RAM 94C and so forth) of microcomputer 94 storing the combustible gas concentration may store only the newest combustible gas concentration.

Furthermore, in the above-described embodiments, heating resistors (left-side heating resistance element (resistor) 331 and right-side heating resistance element (resistor) 332) are enclosed with inner protective layer 350 and outer protective layer 360 and are disposed indirectly within the atmosphere to be detected via inner protective layer 350 and outer protective layer 360. However, the present invention is not limited to such a structure as described above. For example, in the atmosphere to be detected in which such a component as to erode the heating resistance elements is not present, the heating resistors may directly be disposed within the atmosphere to be detected in which the heating resistors are exposed to the atmosphere to be detected with no protective layers.

In addition, gas sensitivity (G1 or G2), in some cases, does not receive an influence due to temperature T according to the kind (material quality, shape, and so forth) of the heating resistors (left-side heating resistor 331 and right-side heating resistor 332). In such a case described above, the gas sensitivity may be a predetermined constant and the combustible gas concentration may correspondingly be calculated. It should be noted that, in the present specification and drawings, hydrogen indicates a hydrogen molecule $H_2$ (viz., hydrogen gas).

This application is based on a prior Japanese Patent Application No. 2007-012831. The entire contents of the Japanese Patent Application No. 2007-012831 with a filing date of Jan. 23, 2007 are hereby incorporated by reference. Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. An apparatus for detecting a combustible gas within an atmosphere to be detected, comprising:
    a plurality of heating resistors including at least first and second heating resistors disposed within the atmosphere to be detected, wherein at least one of the first and second heating resistors functions to detect a gas concentration of the combustible gas within the atmosphere;
    a power supply control section configured to perform a power supply control for the first and second heating resistors in order for the first and second heating resistors to provide resistance values corresponding to mutually different target temperatures;
    a temperature detecting section configured to detect a temperature of the atmosphere to be detected;
    a voltage detecting section configured to detect each of terminal voltages across the first and second heating resistors;
    a humidity calculating section configured to calculate a humidity of the atmosphere to be detected on the basis of the respective terminal voltages detected by the voltage detecting section and the temperature detected by the temperature detecting section;
    a concentration calculating section configured to calculate the gas concentration of the combustible gas within the atmosphere to be detected on the basis of the terminal voltage including at least one of the two terminal voltages detected by the voltage detecting section, the humidity calculated by the humidity calculating section, and the temperature detected by the temperature detecting section;
    a gas concentration storing section configured to store the gas concentration calculated by the concentration calculating section therein; and
    a humidity correcting section configured to calculate a calculated humidity deviation corresponding to a past gas concentration stored in the gas concentration storing section on the basis of a preset correlation between the concentration of the combustible gas and the calculated humidity deviation of the humidity calculating section and to correct the humidity of the atmosphere to be detected calculated by the humidity calculating section using the calculated humidity deviation to calculate a corrected humidity, the concentration calculating section using the corrected humidity calculated by the humidity correcting section for the humidity calculated by the humidity calculating section.

2. The apparatus as claimed in claim 1, wherein the gas concentration storing section stores the concentration of the combustible gas whenever the concentration calculating section calculates the concentration of the combustible gas in the atmosphere to be detected and the humidity correcting section corrects the humidity using a newest concentration of the combustible gas in the atmosphere to be detected from among the gas concentrations stored in the gas concentration storing section.

3. The apparatus as claimed in claim 1, wherein the humidity calculating section comprises voltage ratio calculating section configured to calculate a ratio between the respective terminal voltages across the first and second heating resistors detected by the voltage detecting section for a terminal voltage ratio; a reference terminal voltage ratio calculating section configured to calculate the terminal voltage ratio corresponding to the temperature detected by the temperature detecting section for a reference terminal voltage ratio on the basis of a reference correlation which is a correlation between the temperature of the atmosphere to be detected preset under a situation in which the combustible gas and moisture are absent in the atmosphere to be detected and the terminal voltage ratio; a voltage ratio difference value calculating section configured to calculate a value which subtracts the reference terminal voltage ratio from the terminal voltage ratio for a voltage ratio difference value; and a voltage ratio difference value corresponding humidity calculating section configured to calculate the humidity of the atmosphere to be detected corresponding to the voltage ratio difference value calculated by the voltage ratio difference value calculating section on the basis of a correlation between the humidity of the atmosphere to be detected and the voltage ratio difference value.

4. The apparatus as claimed in claim 1, wherein the apparatus further comprises a detection element including: a semiconductor substrate having a plurality of recess portions formed on a rear surface thereof at a interval of distance to one another; an insulating layer formed on a front surface of the semiconductor substrate; and the first and second heating resistors formed at disposed positions of the plurality of recess portions on a surface of the insulating layer; and a protective layer formed on the surface of the insulating layer to enclose the first and second heating resistors.

5. The apparatus as claimed in claim 1, wherein each of the mutually different target temperatures of the first and second heating resistors ranges from 150° C. to 500° C.

6. The apparatus as claimed in claim 1, wherein a difference between the mutually different target temperatures of the first and second heating resistors is equal to or higher than 50° C.

7. The apparatus as claimed in claim 1, wherein the apparatus further comprises: a temperature determining section configured to determine whether the temperature detected by the temperature detecting section is lower than a predetermined temperature lower limit value; and a temperature corresponding humidity calculating section configured to calculate the humidity of the atmosphere to be detected corresponding to the temperature detected by the temperature detecting section on the basis of a preset correlation between the temperature of the atmosphere to be detected and the humidity, the concentration calculating section calculating the gas concentration of the combustible gas using the humidity calculated by the temperature corresponding humidity calculating section without use of the corrected humidity by the humidity correcting section in a case where the temperature determining section determines that the temperature is lower than the predetermined temperature lower limit value.

8. The apparatus as claimed in claim 7, wherein the humidity calculating section calculates the humidity of the atmosphere to be detected and the humidity correcting section calculates the calculated humidity deviation corresponding to the past gas concentration stored in the gas concentration storing section and calculates the corrected humidity in a case where the temperature determining section determines that the temperature detected by the temperature detecting section is equal to or higher than the predetermined temperature lower limit value.

9. The apparatus as claimed in claim 8, wherein the combustible gas is hydrogen gas and the humidity correcting section calculates the corrected humidity using the calculated humidity deviation from the humidity calculated by the humidity calculating section and the concentration of hydrogen gas ((Dn−1)) which has been stored in the gas concentration storing section one previous time before the present calculation of the concentration of the combustible gas by the concentration calculating section.

10. The apparatus as claimed in claim 9, wherein the humidity correcting section calculates the calculated humidity deviation from the following equation:

$$g = m \times (Dn-1),$$

wherein g denotes the calculated humidity deviation and m denotes a predetermined constant.

11. The apparatus as claimed in claim 10, wherein the humidity correcting section calculates the corrected humidity (HUM) using the following equation:

$$HUM = HUM + HUM(\Delta RV) + m \times (Dn-1),$$

wherein HUM($\Delta RV$) denotes the humidity calculated by the humidity calculating section.

12. The apparatus as claimed in claim 11, wherein the concentration calculating section comprises: a reference terminal voltage calculating section configured to calculate a reference terminal voltage which is one of the terminal voltages across a higher-temperature heating resistor of the first and second heating resistors for which the power supply control is performed, the higher-temperature heating resistor having the resistance value to provide a higher target temperature of the mutually different target temperatures, on the basis of the temperature detected by the temperature detecting section in a case where hydrogen gas which is the combustible gas and moisture are absent in the atmosphere to be detected; a humidity corresponding terminal voltage calculating section configured to calculate a humidity corresponding terminal voltage across the higher-temperature heating resistor in a case where hydrogen gas which is the combustible gas is absent in the atmosphere to be detected but only moisture is present therein on the basis of the humidity calculated by the humidity calculating section and the reference terminal voltage; a gas sensitivity calculating section configured to calculate a gas sensitivity on the basis of the temperature detected by the temperature detecting section; and a gas concentration calculating section configured to calculate the present concentration of hydrogen gas in the atmosphere to be detected on the basis of a difference value between a high-temperature-side terminal voltage across the higher-temperature heating resistor and the humidity corresponding terminal voltage.

13. The apparatus as claimed in claim 12, wherein the concentration calculating section further comprises: a concentration storing section configured to store the present concentration ((Dn)) of hydrogen gas in the atmosphere to be detected in the gas concentration storing section and an increment section configured to increment a counter variable n to indicate the combustible gas detection number of times by one, n denoting a natural number.

14. The apparatus as claimed in claim 11, wherein the concentration calculating section comprises: a detected voltage difference value calculating section configured to calculate a difference value between the detected terminal voltages across the first and second heating resistors for which the power supply control is performed; a reference detected voltage difference value calculating section configured to calculate a reference detected value between the detected terminal voltages across the first and second heating resistors for which the power supply control is performed on the basis of the temperature detected by the temperature detecting section in a case where hydrogen gas which is the combustible gas and moisture are absent in the atmosphere to be detected; a humidity corresponding detected voltage difference value calculating section configured to calculate a humidity corresponding detected voltage difference value which is the detected voltage difference value on the basis of the humidity and the reference detected voltage difference value; a second gas sensitivity calculating section configured to calculate a second sensitivity on the basis of the temperature detected by the temperature detecting section; and a gas concentration calculating section configured to calculate the present concentration of hydrogen gas ((Dn)) in the atmosphere to be detected on the basis of a difference value between the detected voltage difference value and the humidity corresponding detected voltage difference value and the second gas sensitivity.

15. The apparatus as claimed in claim 1, wherein the apparatus further comprises: a saturated aqueous vapor concentration calculating section configured to calculate a saturated aqueous vapor concentration corresponding to the temperature detected by the temperature detecting section on the basis of a predetermined correlation between the temperature of the atmosphere to be detected and the saturated aqueous vapor concentration; a humidity upper limit value setting section configured to compare the saturated aqueous vapor concentration calculated by the saturated aqueous vapor concentration calculating section with the corrected humidity calculated by the humidity correcting section and to set the saturated aqueous vapor concentration for the corrected humidity when the corrected humidity is larger than the saturated aqueous vapor concentration; and a humidity lower limit value setting section configured to determine whether the corrected humidity calculated by the humidity correcting section is smaller than zero and to set the corrected humidity to zero when the corrected humidity is smaller than zero.

16. An apparatus for detecting a combustible gas within an atmosphere to be detected, comprising:
a plurality of heating resistors including at least first and second heating resistors disposed within the atmosphere to be detected, wherein at least one of the first and second heating resistors functions to detect a gas concentration of the combustible gas within the atmosphere;
power supply control means for performing a power supply control for the first and second heating resistors in order for the first and second heating resistors to provide resistance values corresponding to mutually different target temperatures;

temperature detecting means for detecting a temperature of the atmosphere to be detected;

voltage detecting means for detecting each of terminal voltages across the first and second heating resistors;

humidity calculating means for calculating a humidity of the atmosphere to be detected on the basis of the respective terminal voltages detected by the voltage detecting means and the temperature detected by the temperature detecting means;

concentration calculating means for calculating the gas concentration of the combustible gas in the atmosphere to be detected on the basis of the terminal voltage including at least one of the two terminal voltages detected by the voltage detecting means, the humidity calculated by the humidity calculating means, and the temperature detected by the temperature detecting means;

gas concentration storing means for storing the gas concentration calculated by the concentration calculating means therein; and humidity correcting means for calculating a calculated humidity deviation corresponding to a past gas concentration stored in the gas concentration storing means on the basis of a preset correlation between the concentration of the combustible gas and the calculated humidity deviation of the humidity calculating means and to correct the humidity of the atmosphere to be detected calculated by the humidity calculating means using the calculated humidity deviation to calculate a corrected humidity, the concentration calculating means using the corrected humidity calculated by the humidity correcting means for the humidity calculated by the humidity calculating means.

17. A method for detecting a combustible gas within an atmosphere to be detected, comprising:

providing a plurality of heating resistors including first and second heating resistors disposed within the atmosphere to be detected, wherein at least one of the first and second heating resistors functions to detect a gas concentration of the combustible gas within the atmosphere;

performing a power supply control for the first and second heating resistors in order for the first and second heating resistors to provide resistance values corresponding to mutually different target temperatures;

detecting a temperature of the atmosphere to be detected;

detecting each of terminal voltages across the first and second heating resistors;

calculating a humidity of the atmosphere to be detected on the basis of the detected respective terminal voltages and the detected temperature;

calculating a gas concentration of the combustible gas in the atmosphere to be detected on the basis of the terminal voltage including at least one of the detected two terminal voltages, the calculated humidity, and the detected temperature;

storing the calculated gas concentration therein;

calculating a calculated humidity deviation corresponding to a stored past gas concentration on the basis of a preset correlation between the gas concentration of the combustible gas and the calculated humidity deviation; and correcting the calculated humidity of the atmosphere to be detected using the calculated humidity deviation to calculate a corrected humidity, at the concentration calculating, the calculated corrected humidity being used for the calculated humidity at the humidity calculating.

* * * * *